United States Patent
Vaswani et al.

(10) Patent No.: US 11,485,732 B2
(45) Date of Patent: Nov. 1, 2022

(54) COMPOUNDS AND USES THEREOF

(71) Applicant: Foghorn Therapeutics Inc., Cambridge, MA (US)

(72) Inventors: Rishi G. Vaswani, Lexington, MA (US); David S. Huang, Cambridge, MA (US)

(73) Assignee: Foghorn Therapeutics Inc., Cambridge, MA (US)

( * ) Notice: Subject to any disclaimer, the term of this patent is extended or adjusted under 35 U.S.C. 154(b) by 94 days.

(21) Appl. No.: 17/162,103

(22) Filed: Jan. 29, 2021

(65) Prior Publication Data

US 2021/0230154 A1 Jul. 29, 2021

Related U.S. Application Data

(60) Provisional application No. 62/967,359, filed on Jan. 29, 2020.

(51) Int. Cl.
| | | |
|---|---|---|
| *C07D 417/14* | (2006.01) | |
| *A61P 35/02* | (2006.01) | |
| *A61P 35/00* | (2006.01) | |

(52) U.S. Cl.
CPC ............ *C07D 417/14* (2013.01); *A61P 35/00* (2018.01); *A61P 35/02* (2018.01)

(58) Field of Classification Search
CPC .................................................. C07D 417/14
See application file for complete search history.

(56) References Cited

U.S. PATENT DOCUMENTS

| | | |
|---|---|---|
| 2,788,341 A | 4/1957 | Schwyzer |
| 3,717,642 A | 2/1973 | Von Strandtmann |
| 8,946,268 B2 | 2/2015 | Lau et al. |
| 9,353,051 B2 | 5/2016 | Byrd et al. |
| 9,410,943 B2 | 8/2016 | Kadoch et al. |
| 10,105,420 B2 | 10/2018 | Kadoch et al. |
| 10,131,637 B2 | 11/2018 | Abdel-Meguid et al. |
| 10,976,320 B2 | 4/2021 | Dykhuizen et al. |
| 2005/0079512 A1 | 4/2005 | Emerson et al. |
| 2015/0376139 A1 | 12/2015 | Abdel-Meguid et al. |
| 2016/0032402 A1 | 2/2016 | Jagani et al. |
| 2016/0130663 A1 | 5/2016 | Kohno et al. |
| 2016/0200721 A1 | 7/2016 | Yukimasa et al. |
| 2016/0347708 A1 | 12/2016 | Ebright et al. |
| 2018/0086720 A1 | 3/2018 | Albrecht et al. |
| 2018/0328913 A1 | 11/2018 | Kadoch et al. |
| 2020/0206344 A1 | 7/2020 | Kadoch et al. |
| 2021/0038611 A1 | 2/2021 | Anthony et al. |
| 2022/0016083 A1 | 1/2022 | Centore et al. |
| 2022/0119378 A1 | 4/2022 | Anthony et al. |

FOREIGN PATENT DOCUMENTS

| | | | |
|---|---|---|---|
| WO | WO-2015/120320 A1 | 8/2015 | |
| WO | WO-2016/138114 A1 | 9/2016 | |
| WO | WO-2017/150395 A1 | 9/2017 | |
| WO | WO-2018/160636 A1 | 9/2018 | |
| WO | WO-2019/152437 A1 | 8/2019 | |
| WO | WO-2019152437 A1 * | 8/2019 | ........... A61K 31/427 |
| WO | WO-2019/226915 A1 | 11/2019 | |
| WO | WO-2020/035779 A1 | 2/2020 | |
| WO | WO-2020/081556 A2 | 4/2020 | |
| WO | WO-2020/081588 A1 | 4/2020 | |
| WO | WO-2020/106915 A1 | 5/2020 | |
| WO | WO-2020/160100 A1 | 8/2020 | |
| WO | WO-2020/160180 A1 | 8/2020 | |
| WO | WO-2021081032 A1 | 4/2021 | |
| WO | WO-2021/155264 A1 | 8/2021 | |
| WO | WO-2021183218 A1 | 9/2021 | |

OTHER PUBLICATIONS

International Search Report and Written Opinion for International Application No. PCT/US21/15876, dated Apr. 7, 2021 (23 pages).
Kadoch et al., "Reversible Disruption of mSWI/SNF (BAF) Complexes by the SS18-SSX Oncogenic Fusion in Synovial Sarcoma," available in PMC May 16, 2013, published in final edited form as: Cell. 153(1):71-85 (2013) (26 pages).
McBride et al., "Disruption of mammalian SWI/SNF and polycomb complexes in human sarcomas: mechanisms and therapeutic opportunities," J Pathol. 244(5): 638-649 (2018).
Papillon et al., "Discovery of Orally Active Inhibitors of Brahma Homolog (BRM)/SMARCA2 ATPase Activity for the Treatment of Brahma Related Gene 1 (BRG1)/SMARCA4-Mutant Cancers," J Med Chem. 61(22): 10155-72 (2018).
Tikdari et al., "Reaction of 2-Aminothiazoles with 5-Oxazolones," ChemInform. 18(47):Abstract 199 (1987) (1 page).
Zvarec et al., "5-Benzylidenerhodanine and 5-benzylidene-2-4-thiazolidinedione based antibacterials," Bioorg Med Chem Lett. 22(8): 2720-2 (2012).

\* cited by examiner

*Primary Examiner* — Shawquia Jackson
(74) *Attorney, Agent, or Firm* — Clark & Elbing LLP

(57) ABSTRACT

The present disclosure features compounds useful for the treatment of BAF complex-related disorders.

18 Claims, 16 Drawing Sheets

COMPOUNDS AND USES THEREOF

BACKGROUND

The invention relates to compounds useful for modulating BRG1- or BRM-associated factors (BAF) complexes. In particular, the invention relates to compounds useful for treatment of disorders associated with BAF complex function.

Chromatin regulation is essential for gene expression, and ATP-dependent chromatin remodeling is a mechanism by which such gene expression occurs. The human Switch/Sucrose Non-Fermentable (SWI/SNF) chromatin remodeling complex, also known as BAF complex, has two SWI2-like ATPases known as BRG1 (Brahma-related gene-1) and BRM (Brahma). The transcription activator BRG1, also known as ATP-dependent chromatin remodeler SMARCA4, is encoded by the SMARCA4 gene on chromosome 19. BRG1 is overexpressed in some cancer tumors and is needed for cancer cell proliferation. BRM, also known as probable global transcription activator SNF2L2 and/or ATP-dependent chromatin remodeler SMARCA2, is encoded by the SMARCA2 gene on chromosome 9 and has been shown to be essential for tumor cell growth in cells characterized by loss of BRG1 function mutations. Deactivation of BRG and/or BRM results in downstream effects in cells, including cell cycle arrest and tumor suppression.

SUMMARY

The present invention features compounds useful for modulating a BAF complex. In some embodiments, the compounds are useful for the treatment of disorders associated with an alteration in a BAF complex, e.g., a disorder associated with an alteration in one or both of the BRG1 and BRM proteins. The compounds of the invention, alone or in combination with other pharmaceutically active agents, can be used for treating such disorders.

In an aspect, the invention features a compound, N-(1-((4-(6-(2,6-dimethylmorpholino)pyridin-2-yl)thiazol-2-yl)amino)-3-methoxy-1-oxopropan-2-yl)-1-(methylsulfonyl)-1H-pyrrole-3-carboxamide, or a pharmaceutically acceptable salt thereof, having the structure:

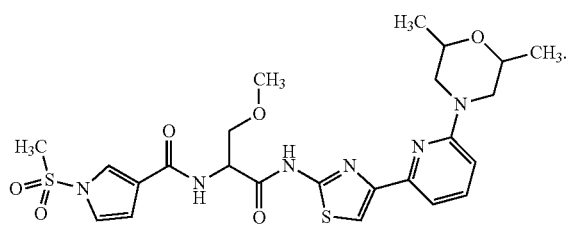 [SMILES: COCC(NC(=O)c1ccn(S(C)(=O)=O)c1)C(=O)Nc1nc(-c2cccc(N3CC(C)OC(C)C3)n2)cs1]

In some embodiments, the compound, or a pharmaceutically acceptable salt thereof, has the structure:

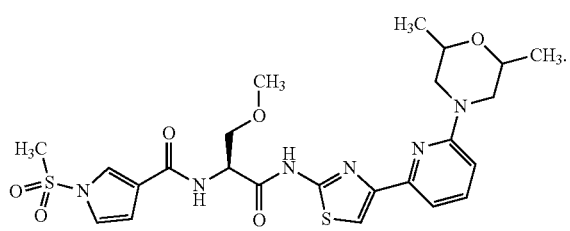 [SMILES: COC[C@H](NC(=O)c1ccn(S(C)(=O)=O)c1)C(=O)Nc1nc(-c2cccc(N3CC(C)OC(C)C3)n2)cs1]

In some embodiments, the compound, or a pharmaceutically acceptable salt thereof, has the structure:

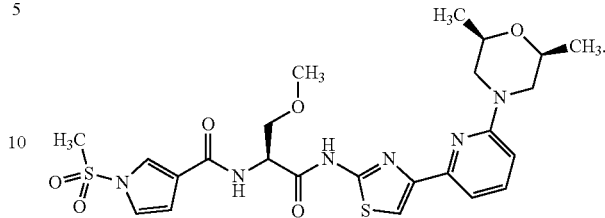

In some embodiments, the compound, or a pharmaceutically acceptable salt thereof, has the structure:

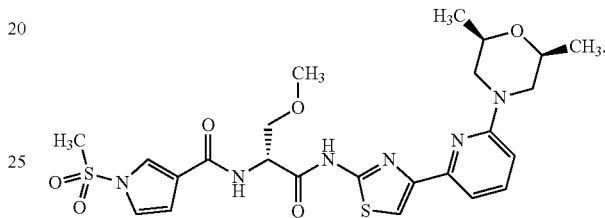

In another aspect, the invention features a compound, N-(1-((4-(6-(2,6-dimethylmorpholino)pyridin-2-yl)thiazol-2-yl)amino)-3-(methoxy-d3)-1-oxopropan-2-yl-3,3-d2)-1-(methylsulfonyl)-1H-pyrrole-3-carboxamide, or a pharmaceutically acceptable salt thereof, having the structure:

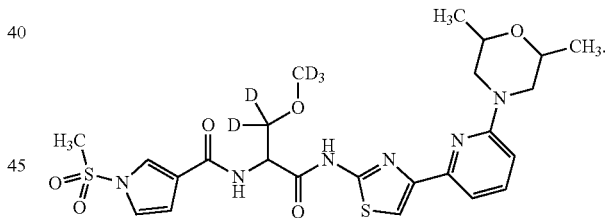

In some embodiments, the compound, or a pharmaceutically acceptable salt thereof, has the structure:

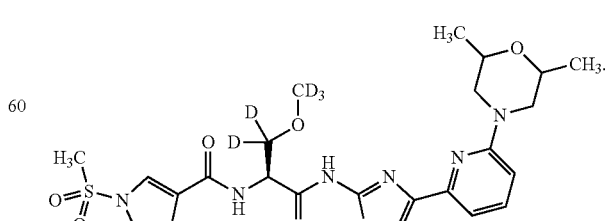

In some embodiments, the compound, or a pharmaceutically acceptable salt thereof, has the structure:

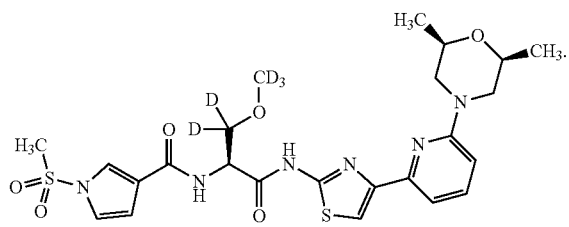 [SMILES: [2H]C([2H])([2H])OC([2H])([2H])[C@H](NC(=O)c1ccn(S(C)(=O)=O)c1)C(=O)Nc1nc(-c2cccc(N3C[C@@H](C)O[C@@H](C)C3)n2)cs1]

In some embodiments, the compound, or a pharmaceutically acceptable salt thereof, has the structure:

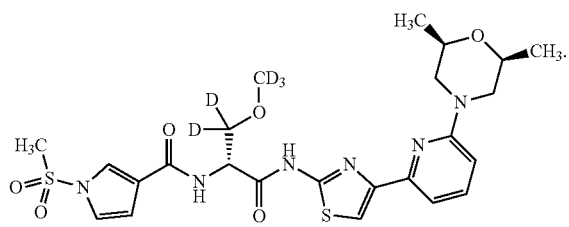 [SMILES: [2H]C([2H])([2H])OC([2H])([2H])[C@@H](NC(=O)c1ccn(S(C)(=O)=O)c1)C(=O)Nc1nc(-c2cccc(N3C[C@@H](C)O[C@@H](C)C3)n2)cs1]

In another aspect, the invention features a pharmaceutical composition including any of the foregoing compounds and a pharmaceutically acceptable excipient.

In another aspect, the invention features a method of decreasing the activity of a BAF complex in a cell or subject. This method includes contacting the cell with, or administering to the subject, an effective amount of any of the foregoing compounds or pharmaceutical compositions.

In another aspect, the invention features a method of inhibiting BRM in a cell or subject. This method includes contacting the cell with, or administering to the subject, an effective amount of any of the foregoing compounds or pharmaceutical compositions.

In another aspect, the invention features a method of inhibiting BRG1 in a cell or subject. This method includes contacting the cell with, or administering to the subject, an effective amount of any of the foregoing compounds or pharmaceutical compositions.

In another aspect, the invention features a method of inhibiting BRM and BRG1 in a cell or subject. This method includes contacting the cell with, or administering to the subject, an effective amount of any of the foregoing compounds or pharmaceutical compositions.

In another aspect, the invention features a method of inducing apoptosis in a cell or subject. This method includes contacting the cell with, or administering to the subject, an effective amount of any of the foregoing compounds or pharmaceutical compositions.

In some embodiments of any of the foregoing methods, the cell is a cancer cell and/or the subject has cancer.

In another aspect, the invention features a method of treating a BAF complex-related disorder in a subject in need thereof. This method includes administering to the subject an effective amount of any of the foregoing compounds or pharmaceutical compositions.

In another aspect, the invention features a method of treating a disorder related to a BRG1 loss of function mutation in a subject in need thereof. This method includes administering to the subject an effective amount of any of the foregoing compounds or pharmaceutical compositions.

In some embodiments, the subject is determined to have a BRG1 loss of function disorder (e.g., the disorder and/or subject has been determined to include cells with a loss of BRG1 function mutation).

In some embodiments of the foregoing methods, the BAF complex-related disorder or disorder related to a BRG1 loss of function mutation is a cancer, a viral infection, Coffin Siris, Neurofibromatosis (e.g., NF-1, NF-2, or Schwannomatosis), or Multiple Meningioma.

In another aspect, the invention features a method of treating cancer in a subject in need thereof. This method includes administering to the subject an effective amount of any of the foregoing compounds or pharmaceutical compositions.

In another aspect, the invention features a method of reducing tumor growth of cancer in a subject in need thereof in need thereof. This method includes administering to the subject an effective amount of any of the foregoing compounds or pharmaceutical compositions.

In another aspect, the invention features a method of suppressing metastatic progression of cancer in a subject in need thereof. This method includes administering an effective amount of any of the foregoing compounds or pharmaceutical compositions.

In another aspect, the invention features a method of suppressing metastatic colonization (e.g., metastatic colonization to the lung and/or brain) of cancer in a subject in need thereof. This method includes administering an effective amount of any of the foregoing compounds or pharmaceutical compositions.

In another aspect, the invention features a method of reducing the level and/or activity of BRG1 and/or BRM in a cancer in a cell or subject in need thereof. This method includes contacting the cell with, or administering to the subject, an effective amount of any of the foregoing compounds or pharmaceutical compositions.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, esophagogastric cancer, esophageal cancer, pancreatic cancer, hepatobiliary cancer, soft tissue sarcoma, ovarian cancer, head and neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, penile cancer, bone cancer, or a hematologic cancer. In some embodiments of any of the foregoing methods, the cancer is esophageal cancer.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, penile cancer, bone cancer, renal cell carcinoma, prostate cancer, or a hematologic cancer. In some embodiments of any of the foregoing methods, the cancer is non-small cell lung cancer.

In some embodiments of any of the foregoing methods, the cancer is melanoma, prostate cancer, breast cancer, bone cancer, renal cell carcinoma, or a hematologic cancer.

In some embodiments, the cancer is melanoma (e.g., uveal melanoma, mucosal melanoma, or cutaneous melanoma). In some embodiments, the cancer is prostate cancer. In some embodiments, the cancer is a hematologic cancer (e.g., multiple myeloma, large cell lymphoma, acute T-cell leukemia, acute myeloid leukemia, myelodysplastic syndrome, immunoglobulin A lambda myeloma, diffuse mixed histiocytic and lymphocytic lymphoma, B-cell lymphoma, acute lymphoblastic leukemia (e.g., T-cell acute lymphoblastic leukemia or B-cell acute lymphoblastic leukemia), diffuse large cell lymphoma, or non-Hodgkin's lymphoma). In some embodiments, the cancer is breast cancer (e.g., an ER positive breast cancer, an ER negative breast cancer, triple positive breast cancer, or triple negative breast cancer). In some embodiments, the cancer is a bone cancer (e.g., Ewing's sarcoma). In some embodiments, the cancer is a renal cell carcinoma (e.g., a Microphthalmia Transcription Factor (MITF) family translocation renal cell carcinoma (tRCC)).

In some embodiments, the cancer expresses BRG1 and/or BRM protein and/or the cell or subject has been identified as expressing BRG1 and/or BRM. In some embodiments, the cancer expresses BRG1 protein and/or the cell or subject has been identified as expressing BRG1. In some embodiments, the cancer expresses BRM protein and/or the cell or subject has been identified as expressing BRM. In some embodiments, the subject or cancer has and/or has been identified as having a BRG1 loss of function mutation. In some embodiments, the subject or cancer has and/or has been identified as having a BRM loss of function mutation.

In some embodiments of any of the foregoing methods, the cancer has or has been determined to have one or more BRG1 mutations (e.g., homozygous mutations). In some embodiments, the one or more BRG1 mutations includes a mutation in the ATPase catalytic domain of the protein. In some embodiments, the one or more BRG1 mutations include a deletion at the C-terminus of BRG1.

In some embodiments of any of the foregoing methods, the cancer does not have, or has been determined not to have, an epidermal growth factor receptor (EGFR) mutation. In some embodiments of any of the foregoing methods, the cancer does not have, or has been determined not to have, an anaplastic lymphoma kinase (ALK) driver mutation. In some embodiments of any of the foregoing methods, the cancer has, or has been determined to have, a KRAS mutation.

In some embodiments the cancer has, or has been determined to have, a mutation in GNAQ. In some embodiments the cancer has, or has been determined to have, a mutation in GNA11. In some embodiments the cancer has, or has been determined to have, a mutation in PLCB4. In some embodiments the cancer has, or has been determined to have, a mutation in CYSLTR2. In some embodiments the cancer has, or has been determined to have, a mutation in BAP1. In some embodiments the cancer has, or has been determined to have, a mutation in SF3B1. In some embodiments the cancer has, or has been determined to have, a mutation in EIF1AX. In some embodiments the cancer has, or has been determined to have, a TFE3 translocation. In some embodiments the cancer has, or has been determined to have, a TFEB translocation. In some embodiments the cancer has, or has been determined to have, a MITF translocation. In some embodiments the cancer has, or has been determined to have, an EZH2 mutation. In some embodiments the cancer has, or has been determined to have, a SUZ12 mutation. In some embodiments the cancer has, or has been determined to have, an EED mutation.

In some embodiments, the cancer is metastatic. For example, the cancer includes cells exhibiting migration and/or invasion of migrating cells and/or includes cells exhibiting endothelial recruitment and/or angiogenesis. The metastatic cancer may be spread via seeding the surface of the peritoneal, pleural, pericardial, or subarachnoid spaces. Alternatively, the metastatic cancer may be spread via the lymphatic system, or spread hematogenously. In some embodiments, the cancer is a cell migration cancer (e.g., a non-metastatic cell migration cancer).

In some embodiments of any of the foregoing methods, the cancer is drug resistant (e.g., the cancer has been determined to be resistant, or likely to be resistant, to chemotherapeutic or cytotoxic agents such as by genetic markers, or is likely to be resistant, to chemotherapeutic or cytotoxic agents such as a cancer that has failed to respond to a chemotherapeutic or cytotoxic agent) and/or has failed to respond to a prior therapy (e.g., a chemotherapeutic or cytotoxic agent, immunotherapy, surgery, radiotherapy, thermotherapy, or photocoagulation, or a combination thereof).

In some embodiments, the cancer is resistant to and/or has failed to respond to vemurafenib, dacarbazine, a CTLA4 inhibitor, a PD1 inhibitor, interferon therapy, a BRAF inhibitor, a MEK inhibitor, radiotherapy, temozolimide, irinotecan, a CAR-T therapy, herceptin, perjeta, tamoxifen, xeloda, docetaxol, platinum agents such as carboplatin, taxanes such as paclitaxel and docetaxel, ALK inhibitors, MET inhibitors, alimta, abraxane, doxorubicin, gemcitabine, avastin, halaven, neratinib, a PARP inhibitor, brilanestrant, an mTOR inhibitor, topotecan, gemzar, a VEGFR2 inhibitor, a folate receptor antagonist, demcizumab, fosbretabulin, or a PDL1 inhibitor, or combinations thereof.

In some embodiments of any of the foregoing methods, the cancer is resistant to and/or has failed to respond to dacarbazine, temozolomide, cisplatin, treosulfan, fotemustine, IMCgp100, a CTLA-4 inhibitor (e.g., ipilimumab), a PD-1 inhibitor (e.g., nivolumab or pembrolizumab), a PD-L1 inhibitor (e.g., atezolizumab, avelumab, or durvalumab), a mitogen-activated protein kinase, (MEK) inhibitor (e.g., selumetinib, binimetinib, or tametinib), and/or a protein kinase C (PKC) inhibitor (e.g., sotrastaurin or IDE196).

In some embodiments of any of the foregoing methods, the cancer is resistant to and/or failed to respond to a previously administered therapeutic used for the treatment of uveal melanoma, e.g., a MEK inhibitor or PKC inhibitor. For example, in some embodiments, the cancer is resistant to and/or failed to respond to a mitogen-activated protein kinase (MEK) inhibitor (e.g., selumetinib, binimetinib, or tametinib), and/or a protein kinase C (PKC) inhibitor (e.g., sotrastaurin or IDE196).

In some embodiments, the method further includes administering to the subject or contacting the cell with an anticancer therapy, e.g., a chemotherapeutic or cytotoxic agent, immunotherapy, surgery, radiotherapy, thermotherapy, or photocoagulation, or combinations thereof. In some embodiments, the anticancer therapy is a chemotherapeutic or cytotoxic agent, e.g., an antimetabolite, antimitotic, antitumor antibiotic, asparagine-specific enzyme, bisphosphonates, antineoplastic, alkylating agent, DNA-Repair enzyme inhibitor, histone deacetylase inhibitor, corticosteroid, demethylating agent, immunomodulatory, janus-associated kinase inhibitor, phosphinositide 3-kinase inhibitor, proteasome inhibitor, or tyrosine kinase inhibitor, or combinations thereof.

In some embodiments, the compound of the invention is used in combination with another anti-cancer therapy used for the treatment of uveal melanoma such as surgery, a MEK inhibitor, and/or a PKC inhibitor, or combinations thereof. For example, in some embodiments, the method further comprises performing surgery prior to, subsequent to, or at the same time as administration of the compound of the invention. In some embodiments, the method further comprises administration of a MEK inhibitor (e.g., selumetinib, binimetinib, or tametinib) and/or a PKC inhibitor (e.g., sotrastaurin or IDE196) prior to, subsequent to, or at the same time as administration of the compound of the invention.

In some embodiments, the anticancer therapy and the compound of the invention are administered within 28 days (e.g., within 21 days, within 14 days, or within 7 days) of each other and each in an amount that together are effective to treat the subject.

In another aspect, the disclosure provides a method for treating a viral infection in a subject in need thereof. This method includes administering to the subject an effective amount of any of the foregoing compounds, or pharmaceutical compositions. In some embodiments, the viral infection is an infection with a virus of the Retroviridae family such as the lentiviruses (e.g., Human immunodeficiency virus (HIV)) and deltaretroviruses (e.g., human T cell leukemia virus I (HTLV-I), human T cell leukemia virus II (HTLV-II)), a virus of the Hepadnaviridae family (e.g., hepatitis B virus (HBV)), a virus of the Flaviviridae family (e.g., hepatitis C virus (HCV)), a virus of the Adenoviridae family (e.g., Human Adenovirus), a virus of the Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), a virus of the Papillomaviridae family (e.g., Human Papillomavirus (HPV, HPV E1)), a virus of the Parvoviridae family (e.g., Parvovirus B19), a virus of the Polyomaviridae family (e.g., JC virus and BK virus), a virus of the Paramyxoviridae family (e.g., Measles virus), or a virus of the Togaviridae family (e.g., Rubella virus).

In some embodiments of any of the foregoing methods, the effective amount of the compound reduces the level and/or activity of BRG1 by at least 5% (e.g., at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%) as compared to a reference.

In some embodiments of any of the foregoing methods, the effective amount of the compound reduces the level and/or activity of BRG1 by at least 5% (e.g., at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%) as compared to a reference for at least 12 hours (e.g., at least 14 hours, at least 16 hours, at least 18 hours, at least 20 hours, at least 22 hours, at least 24 hours, at least 30 hours, at least 36 hours, at least 48 hours, at least 72 hours, at least 4 days, at least 5 days, at least 6 days, at least 7 days, at least 14 days, at least 21 days, at least 28 days, or more).

In some embodiments of any of the foregoing methods, the effective amount of the compound reduces the level and/or activity of BRM by at least 5% (e.g., at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%) as compared to a reference.

In some embodiments of any of the foregoing methods, the effective amount of the compound reduces the level and/or activity of BRM by at least 5% (e.g., at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%) as compared to a reference for at least 12 hours (e.g., at least 14 hours, at least 16 hours, at least 18 hours, at least 20 hours, at least 22 hours, at least 24 hours, at least 30 hours, at least 36 hours, at least 48 hours, at least 72 hours, at least 4 days, at least 5 days, at least 6 days, at least 7 days, at least 14 days, at least 21 days, at least 28 days, or more).

In some embodiments, the effective amount of the compound of the invention is an amount effective to inhibit metastatic colonization of the cancer to the liver and/or brain.

Chemical Terms

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically-labeled compounds (e.g., those labeled with $^3H$ and $^{14}C$)) can be useful in compound or substrate tissue distribution assays. Tritiated (i.e., $^3H$) and carbon-14 (i.e., $^{14}C$)) isotopes can be useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements). In some embodiments, one or more hydrogen atoms are replaced by $^2H$ or $^3H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

In this application, unless otherwise clear from context, (i) the term "a" may be understood to mean "at least one"; (ii) the term "or" may be understood to mean "and/or"; and (iii) the terms "comprising" and "including" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term "BAF complex" refers to the BRG1- or HBRM-associated factors complex in a human cell.

As used herein, the term "BAF complex-related disorder" refers to a disorder that is caused or affected by the level of activity of a BAF complex.

As used herein, the term "BRG1 loss of function mutation" refers to a mutation in BRG1 that leads to the protein having diminished activity (e.g., at least 1% reduction in BRG1 activity, for example 2%, 5%, 10%, 25%, 50%, or 100% reduction in BRG1 activity). Exemplary BRG1 loss of function mutations include, but are not limited to, a homozygous BRG1 mutation and a deletion at the C-terminus of BRG1.

As used herein, the term "BRG1 loss of function disorder" refers to a disorder (e.g., cancer) that exhibits a reduction in BRG1 activity (e.g., at least 1% reduction in BRG1 activity, for example 2%, 5%, 10%, 25%, 50%, or 100% reduction in BRG1 activity).

The term "cancer" refers to a condition caused by the proliferation of malignant neoplastic cells, such as tumors, neoplasms, carcinomas, sarcomas, leukemias, and lymphomas.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

The term "CTLA-4 inhibitor," as used herein, refers to a compound such as an antibody capable of inhibiting the activity of the protein that in humans is encoded by the CTLA4 gene. Known CTLA-4 inhibitors include ipilimumab.

By "determining the level" of a protein or RNA is meant the detection of a protein or an RNA, by methods known in the art, either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure RNA levels are known in the art and include, but are not limited to, quantitative polymerase chain reaction (qPCR) and Northern blot analyses.

By a "decreased level" or an "increased level" of a protein or RNA is meant a decrease or increase, respectively, in a protein or RNA level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, µg/mL, ng/mL) or percentage relative to total protein in a sample.

By "decreasing the activity of a BAF complex" is meant decreasing the level of an activity related to a BAF complex, or a related downstream effect. A non-limiting example of decreasing an activity of a BAF complex is Sox2 activation. The activity level of a BAF complex may be measured using any method known in the art, e.g., the methods described in Kadoch et al. Cell, 2013, 153, 71-85, the methods of which are herein incorporated by reference.

As used herein, the term "derivative" refers to naturally-occurring, synthetic, and semi-synthetic analogues of a compound, peptide, protein, or other substance described herein. A derivative of a compound, peptide, protein, or other substance described herein may retain or improve upon the biological activity of the original material.

A cancer "determined to be drug resistant," as used herein, refers to a cancer that is drug resistant, based on unresponsiveness or decreased responsiveness to a chemotherapeutic agent, or is predicted to be drug resistant based on a prognostic assay (e.g., a gene expression assay).

By a "drug resistant" is meant a cancer that does not respond, or exhibits a decreased response to, one or more chemotherapeutic agents (e.g., any agent described herein).

As used herein, the term "failed to respond to a prior therapy" or "refractory to a prior therapy," refers to a cancer that progressed despite treatment with the therapy.

As used herein, the term "inhibiting BRM" and/or "inhibiting BRG1" refers to blocking or reducing the level or activity of the ATPase catalytic binding domain or the bromodomain of the protein. BRM and/or BRG1 inhibition may be determined using methods known in the art, e.g., a BRM and/or BRG1 ATPase assay, a Nano DSF assay, or a BRM and/or BRG1 Luciferase cell assay.

As used herein, the term "LXS196," also known as IDE196, refers to the PKC inhibitor having the structure:

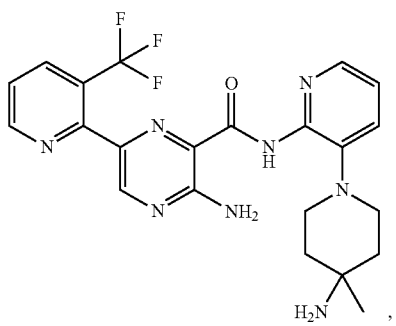 [SMILES: CC1(N)CCN(c2cccnc2NC(=O)c2nc(-c3ncccc3C(F)(F)F)cnc2N)CC1]

or a pharmaceutically acceptable salt thereof.

As used herein, "metastatic nodule" refers to an aggregation of tumor cells in the body at a site other than the site of the original tumor.

As used herein, "metastatic cancer" refers to a tumor or cancer in which the cancer cells forming the tumor have a high potential to or have begun to, metastasize, or spread from one location to another location or locations within a subject, via the lymphatic system or via haematogenous spread, for example, creating secondary tumors within the subject. Such metastatic behavior may be indicative of malignant tumors. In some cases, metastatic behavior may be associated with an increase in cell migration and/or invasion behavior of the tumor cells.

Examples of cancers that can be defined as metastatic include but are not limited to lung cancer (e.g., non-small cell lung cancer), breast cancer, ovarian cancer, colorectal cancer, biliary tract cancer, bladder cancer, brain cancer including glioblastomas and medullablastomas, cervical cancer, choriocarcinoma, endometrial cancer, esophageal cancer, gastric cancer, hematological neoplasms, multiple myeloma, leukemia, intraepithelial neoplasms, liver cancer, lymphomas, neuroblastomas, oral cancer, pancreatic cancer, prostate cancer, sarcoma, skin cancer including melanoma, basocellular cancer, squamous cell cancer, testicular cancer, stromal tumors, germ cell tumors, thyroid cancer, and renal cancer.

"Non-metastatic cell migration cancer" as used herein refers to cancers that do not migrate via the lymphatic system or via haematogenous spread.

The term "PD-1 inhibitor," as used herein, refers to a compound such as an antibody capable of inhibiting the activity of the protein that in humans is encoded by the PDCD1 gene. Known PD-1 inhibitors include nivolumab, pembrolizumab, pidilizumab, BMS 936559, and atezolizumab.

The term "PD-L1 inhibitor," as used herein, refers to a compound such as an antibody capable of inhibiting the activity of the protein that in humans is encoded by the CD274 gene. Known PD-L1 inhibitors include atezolizumab and durvalumab.

The term "pharmaceutical composition," as used herein, represents a composition containing a compound described herein formulated with a pharmaceutically acceptable excipient and appropriate for administration to a mammal, for example a human. Typically, a pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers to any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration.

As used herein, the term "pharmaceutically acceptable salt" means any pharmaceutically acceptable salt of a compound described herein. Pharmaceutically acceptable salts of any of the compounds described herein may include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be, e.g., acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

"Progression-free survival" as used herein, refers to the length of time during and after medication or treatment during which the disease being treated (e.g., cancer) does not get worse.

"Proliferation" as used in this application involves reproduction or multiplication of similar forms (cells) due to constituting (cellular) elements.

By a "reference" is meant any useful reference used to compare protein or RNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound of the invention; a sample from a subject that has been treated by a compound of the invention; or a sample of a purified protein or RNA (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound of the invention. In preferred embodiments, the reference sample, standard, or level is matched to the sample subject sample by at least one of the following criteria: age, weight, sex, disease stage, and overall health. A standard curve of levels of a purified protein or RNA, e.g., any described herein, within the normal reference range can also be used as a reference.

As used herein, "slowing the spread of metastasis" refers to reducing or stopping the formation of new loci; or reducing, stopping, or reversing the tumor load.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean therapeutic treatment or any measures whose object is to slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total); an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. Compounds of the invention may also be used to "prophylactically treat" or "prevent" a disorder, for example, in a subject at increased risk of developing the disorder.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

DETAILED DESCRIPTION

Figure 1:
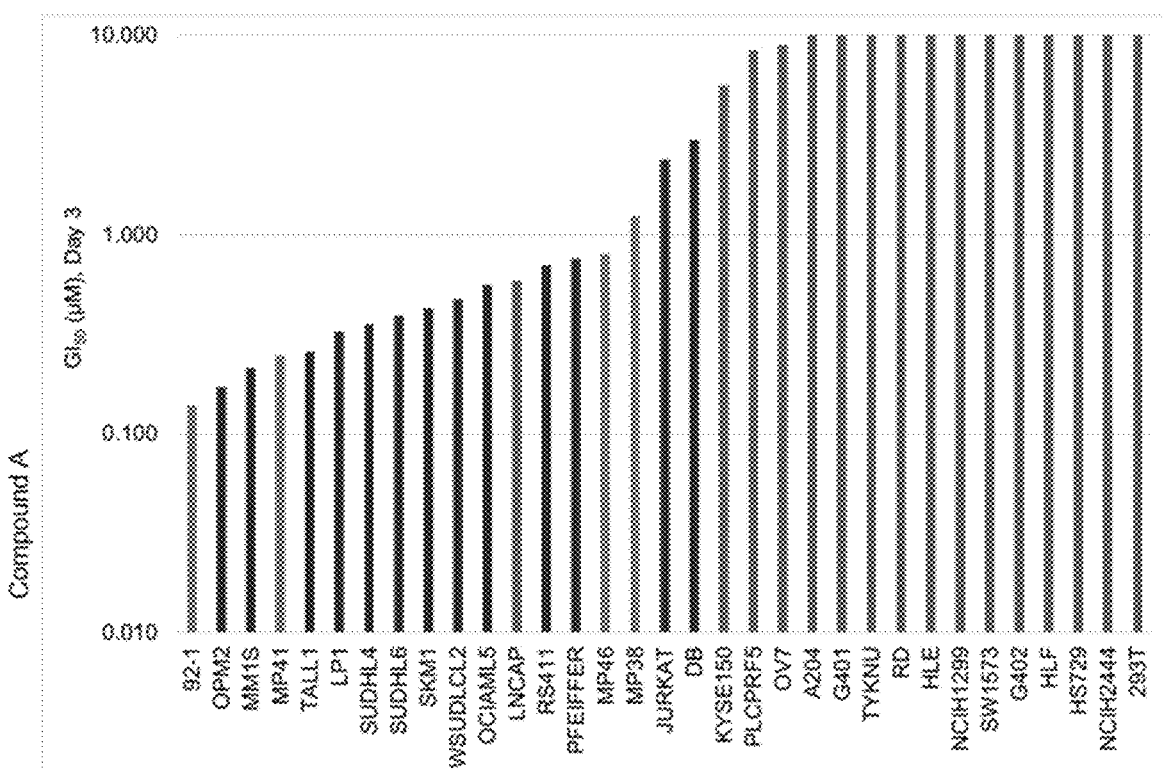
FIG. 1 is a graph illustrating inhibition of cell proliferation of several cancer cell lines by a BRG1/BRM inhibitor (Compound A).

The present disclosure features compounds useful for the inhibition of BRG1 and/or BRM. These compounds may be used to modulate the activity of a BAF complex, for example, for the treatment of a BAF-related disorder, such as cancer. Exemplary compounds, or pharmaceutically acceptable salts thereof, described herein include compounds having the structure:

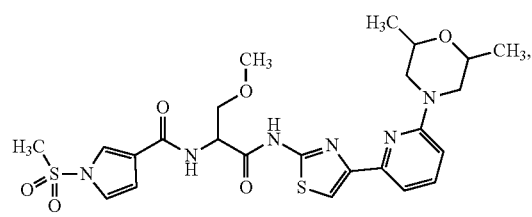

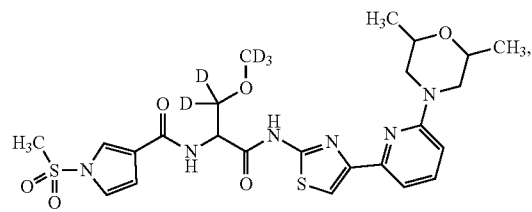

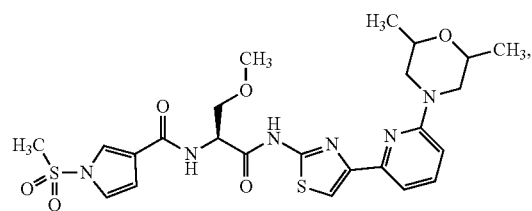

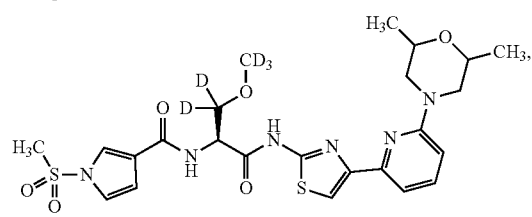

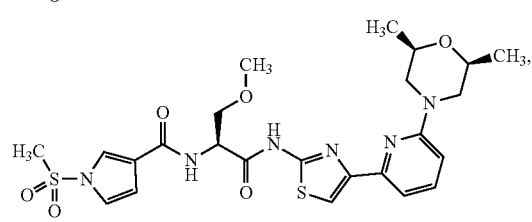

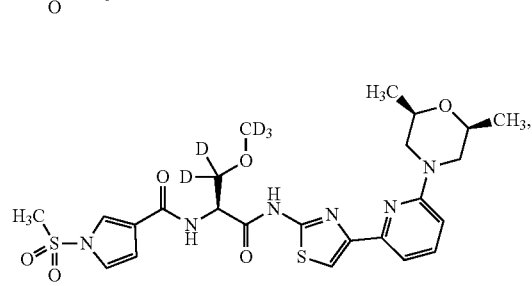

-continued

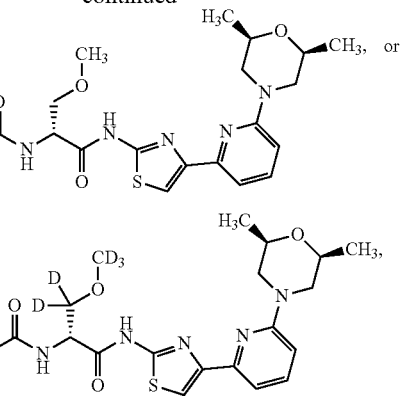

Other embodiments, as well as exemplary methods for the synthesis of production of these compounds, are described herein.

Pharmaceutical Uses

The compounds described herein are useful in the methods of the invention and, while not bound by theory, are believed to exert their ability to modulate the level, status, and/or activity of a BAF complex, i.e., by inhibiting the activity of the BRG1 and/or BRM proteins within the BAF complex in a mammal. BAF complex-related disorders include, but are not limited to, BRG1 loss of function mutation-related disorders.

An aspect of the present invention relates to methods of treating disorders related to BRG1 loss of function mutations such as cancer (e.g., non-small cell lung cancer, colorectal cancer, bladder cancer, cancer of unknown primary, glioma, breast cancer, melanoma, non-melanoma skin cancer, endometrial cancer, or penile cancer) in a subject in need thereof. In some embodiments, the present invention relates to methods of treating melanoma (e.g., uveal melanoma), prostate cancer, breast cancer, bone cancer, renal cell carcinoma, or a hematologic cancer.

In some embodiments, the compound is administered in an amount and for a time effective to result in one or more (e.g., two or more, three or more, four or more) of: (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, (i) increased progression free survival of subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating fora population the average length of survival following initiation of treatment with the compound of the invention. An increase in average survival time of a population may also be measured, for example, by calculating for a population the average length of survival following completion of a first round of treatment with a pharmaceutically acceptable salt of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of the invention. A decrease in the mortality rate of a population may also be measured, for example, by calculating for a population the average number of disease-related deaths per unit time following completion of a first round of treatment with a pharmaceutically acceptable salt of the invention.

Exemplary cancers that may be treated by the invention include, but are not limited to, non-small cell lung cancer, small-cell lung cancer, colorectal cancer, bladder cancer, glioma, breast cancer, melanoma, non-melanoma skin cancer, endometrial cancer, esophagogastric cancer, esophageal cancer, pancreatic cancer, hepatobiliary cancer, soft tissue sarcoma, ovarian cancer, head and neck cancer, renal cell carcinoma, bone cancer, non-Hodgkin lymphoma, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, hematologic cancer, and penile cancer.

Combination Formulations and Uses Thereof

The compounds of the invention can be combined with one or more therapeutic agents. In particular, the therapeutic agent can be one that treats or prophylactically treats any cancer described herein.

Combination Therapies

A compound of the invention can be used alone or in combination with an additional therapeutic agent, e.g., other agents that treat cancer or symptoms associated therewith, or in combination with other types of treatment to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., Neurology 65:S3-S6, 2005). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, Adriamycin® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine;

bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), ABraxane®, cremophor-free, albumin-engineered nanoparticle formulation of paclitaxel (American Pharmaceutical Partners, Schaumberg, Ill.), and Taxotere® doxetaxel (Rhone-Poulenc Rorer, Antony, France); chlorambucil; Gemzar gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al. (1999) Proc ASCO 18:233a and Douillard et al. (2000) Lancet 355:1041-7.

In some embodiments, the second therapeutic agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (Avastin®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include Rituxan (Rituximab); Zenapax (Daclizumab); Simulect (Basiliximab); Synagis (Palivizumab); Remicade (Infliximab); Herceptin (Trastuzumab); Mylotarg (Gemtuzumab ozogamicin); Campath (Alemtuzumab); Zevalin (Ibritumomab tiuxetan); Humira (Adalimumab); Xolair (Omalizumab); Bexxar (Tositumomab-I-131); Raptiva (Efalizumab); Erbitux (Cetuximab); Avastin (Bevacizumab); Tysabri (Natalizumab); Actemra (Tocilizumab); Vectibix (Panitumumab); Lucentis (Ranibizumab); Soliris (Eculizumab); Cimzia (Certolizumab pegol); Simponi (Golimumab); Ilaris (Canakinumab); Stelara (Ustekinumab); Arzerra (Ofatumumab); Prolia (Denosumab); Numax (Motavizumab); ABThrax (Raxibacumab); Benlysta (Belimumab); Yervoy (Ipilimumab); Adcetris (Brentuximab Vedotin); Perjeta (Pertuzumab); Kadcyla (Ado-trastuzumab emtansine); and Gazyva (Obinutuzumab). Also included are antibody-drug conjugates.

The second agent may be a therapeutic agent which is a non-drug treatment. For example, the second therapeutic agent is radiation therapy, cryotherapy, hyperthermia and/or surgical excision of tumor tissue.

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody such as ipilimumab/Yervoy or tremelimumab). In some embodiments, the inhibitor of checkpoint is an inhibitor (e.g., an inhibitory antibody or small molecule inhibitor) of PD-1 (e.g., nivolumab/Opdivo®; pembrolizumab/Keytruda®; pidilizumab/CT-011). In some embodiments, the inhibitor of checkpoint is an inhibitor (e.g., an inhibitory antibody or small molecule inhibitor) of PDL1 (e.g., MPDL3280A/RG7446; MED14736; MSB0010718C; BMS 936559). In some embodiments, the inhibitor of checkpoint is an inhibitor (e.g., an inhibitory antibody or Fc fusion or small molecule inhibitor) of PDL2 (e.g., a PDL2/Ig fusion protein such as AMP 224). In some embodiments, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK1, CHK2, A2aR, B-7 family ligands, or a combination thereof.

In some embodiments, the compound of the invention is used in combination with another anti-cancer therapy used for the treatment of uveal melanoma such as surgery, a MEK inhibitor, and/or a PKC inhibitor, or a combination thereof. For example, in some embodiments, the method further comprises performing surgery prior to, subsequent to, or at the same time as administration of the compound of the invention. In some embodiments, the method further comprises administration of a MEK inhibitor (e.g., selumetinib, binimetinib, or tametinib) and/or a PKC inhibitor (e.g., sotrastaurin or IDE196) prior to, subsequent to, or at the same time as administration of the compound of the invention.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Pharmaceutical Compositions

The compounds of the invention are preferably formulated into pharmaceutical compositions for administration to a mammal, preferably, a human, in a biologically compatible form suitable for administration in vivo. Accordingly, in an aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard- or soft-shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, and wafers.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003, 20th ed.) and in The United States Pharmacopeia: The National Formulary (USP 24 NF19), published in 1999. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg (measured as the solid form).

Alternatively, the dosage amount can be calculated using the body weight of the patient. For example, the dose of a compound, or pharmaceutical composition thereof, administered to a patient may range from 0.1-50 mg/kg.

EXAMPLES

The abbreviations below are used throughout the examples section.

Boc tert-butoxycarbonyl

DCM dichloromethane

DIPEA or DIEA N.N-diisopropylethylamine

DMF N.N-dimethylformamide

DMSO dimethyl sulfoxide

EDCI N-(3-dimethylaminopropyl)-N'-ethylcarbodiimide hydrochloride

EEDQ 2-ethoxy-1-ethoxycarbonyl-1,2-dihydroquinoline

EtOH ethyl alcohol h or hr hour

HOBt or HOBT 1-hydroxybenzotriazole hydrate

MeOH methyl alcohol

MsCl methanesulfonyl chloride

NaHMDS sodium bis(trimethylsilyl)amide

PdCl$_2$(dtbpf) dichloro[1,1'-bis(di-t-butylphosphino)ferrocene]palladium(II)

THF tetrahydrofuran

TMSCHN$_2$ (diazomethyl)trimethylsilane

Example 1. Preparation of N—((S)-1-((4-(6-(cis-2,6-dimethylmorpholino)pyridin-2-yl)thiazol-2-yl)amino)-3-methoxy-1-oxopropan-2-yl)-1-(methylsulfonyl)-1H-pyrrole-3-carboxamide N—((S)-1-((4-(6-(cis-2,6-dimethylmorpholino)pyridin-2-yl)thiazol-2-yl)amino)-3-methoxy-1-oxopropan-2-yl)-1-(methylsulfonyl)-1H-pyrrole-3-carboxamide was synthesized as shown in Scheme 1 below.

Scheme 1.
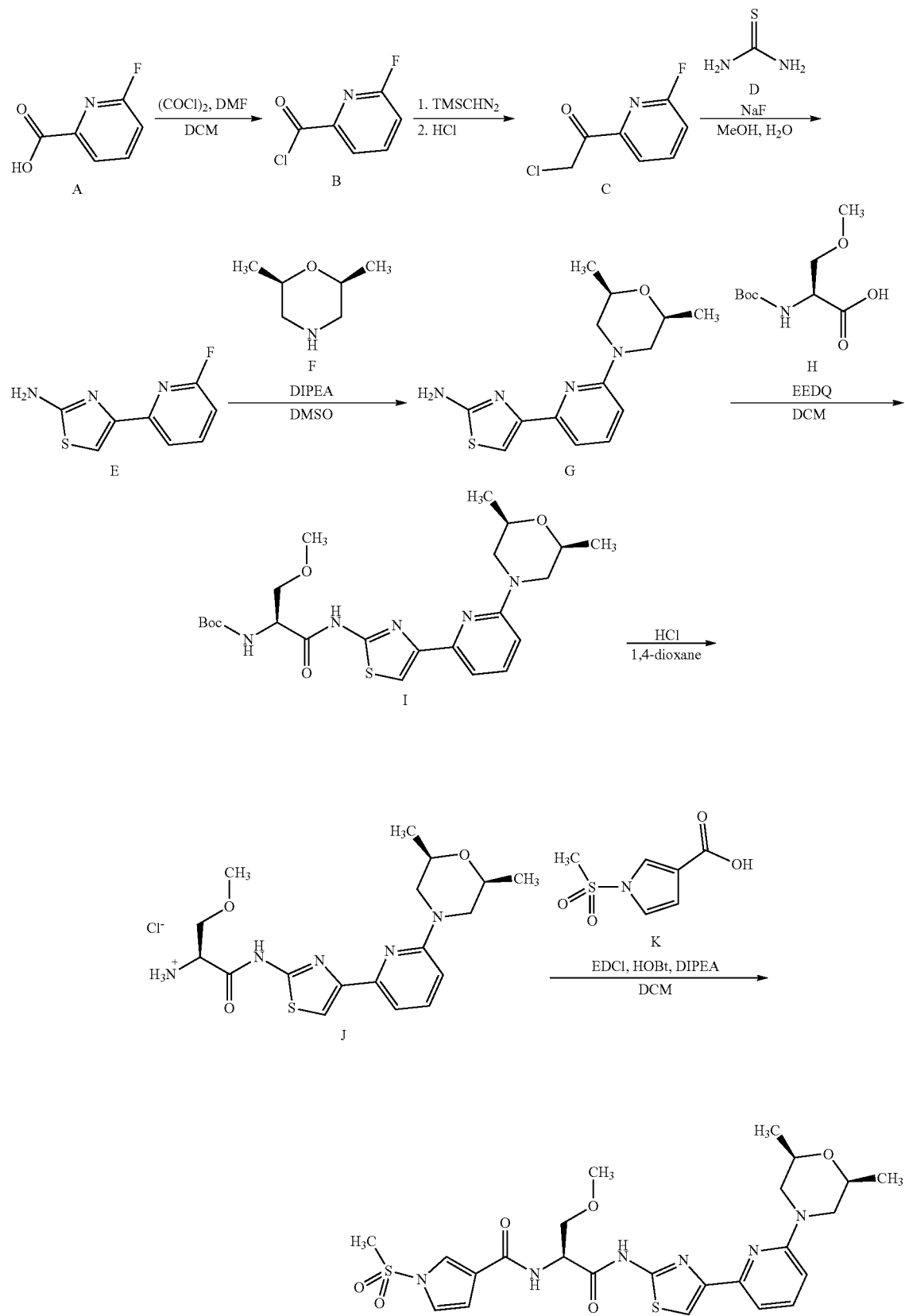

Step 1: Preparation of 6-fluoropyridine-2-carbonyl chloride (Intermediate B)

B

To a cooled (0° C.) solution of 6-fluoropyridine-2-carboxylic acid (50.0 g, 354 mmol) in dichloromethane (500 mL) and N,N-dimethylformamide (0.26 mL, 3.54 mmol) was added oxalyl chloride (155 mL, 1.77 mol). After complete addition of oxalyl chloride, the reaction mixture was warmed to room temperature. After 0.5 hours, the mixture was concentrated under vacuum to give Intermediate B (56.50 g) as a white solid, which was used in the next step without further purification.

Step 2: Preparation of 2-chloro-1-(6-fluoro-2-pyridyl)ethenone (Intermediate C)

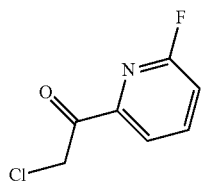

C

To a cooled (0° C.) mixture of Intermediate B (56.0 g, 351 mmol) in 1,4-dioxane (800 mL) was added in a dropwise manner a solution of 2M trimethylsilyl diazomethane in hexanes (351 mL, 702 mmol). The resulting reaction mixture was stirred at 25° C. for 10 h. The reaction mixture was subsequently quenched with a solution of 4M HCl in 1,4-dioxane (500 mL, 2.0 mol). After stirring for 2 h, the reaction solution was concentrated under vacuum to give an oil. The residue was diluted with saturated aqueous NaHCO$_3$ and extracted three times with ethyl acetate. The combined organic layers were washed twice with brine, dried over Na$_2$SO$_4$, filtered, and concentrated under reduced pressure to give Intermediate C (35.5 g) as a white solid, which was used to next step directly. LCMS (ESI) m/z: [M+H]$^+$=173.8.

Step 3: Preparation of 4-(6-fluoro-2-pyridyl)thiazol-2-amine (Intermediate E)

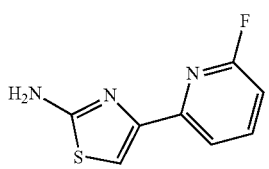

E

To a solution of Intermediate C (35.5 g, 205 mmol) and thiourea (14.0 g, 184 mmol) in a mixture of methanol (250 mL) and water (250 mL) at room temperature was added NaF (3.56 g, 84.8 mmol). After stirring for 0.5 h, the reaction mixture was partially concentrated under vacuum to remove MeOH, and the resulting solution was acidified to pH ~3 with aqueous 2M HCl. After 15 minutes, the solution was extracted three times with ethyl acetate. The organic layers were discarded and the aqueous phase was alkalized with saturated aqueous NaHCO$_3$ and stirred for 30 minutes, and extracted three times with ethyl acetate. The combined organic layers were washed three times with brine, dried over Na$_2$SO$_4$, filtered, and concentrated under reduced pressure. The residue was triturated with petroleum ether and stirred at 25° C. for 10 minutes and filtered. The resultant solids were dried under vacuum to give Intermediate E (28.0 g, 143 mmol, 70.1% yield, 100% purity) as a white solid.

LCMS (ESI) m/z: [M+H]$^+$=195.8.

$^1$H NMR (400 MHz, DMSO-d6) δ 8.00-7.96 (m, 1H), 7.72 (d, J=7.2 Hz, 1H), 7.24 (s, 1H), 7.16 (s, 2H), 7.02 (d, J=8.0 Hz, 1H).

Step 4: Preparation of 4-[6-[cis-2,6-dimethylmorpholin-4-yl]-2-pyridyl]thiazol-2-amine (Intermediate G)

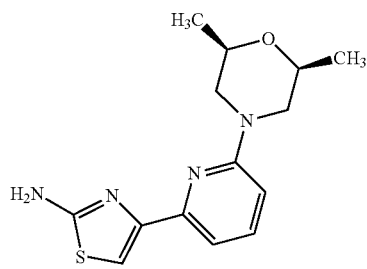

G

Ten separate mixtures of Intermediate E (2.00 g, 10.3 mmol), cis-2,6-dimethylmorpholine (3.54 g, 30.7 mmol), and DIPEA (5.35 mL, 30.7 mmol) in dimethyl sulfoxide (10 mL) were stirred in parallel at 120° C. under N$_2$ atmosphere. After 36 h, the reaction mixtures were combined and added dropwise to water. The resulting suspension was filtered and the filter cake was washed three times with water and once with petroleum ether, then dried over under reduced pressure to give Intermediate G (25.5 g, 87.8 mmol, 95.2% yield) as a yellow solid.

LCMS (ESI) m/z: [M+H]$^+$=291.2.

$^1$H NMR (400 MHz, DMSO-d6) δ 7.56-7.54 (m, 1H), 7.17 (s, 1H), 7.13 (d, J=7.6 Hz, 1H), 7.01 (s, 2H), 6.72 (d, J=8.8 Hz, 1H), 4.26-4.15 (m, 2H), 3.67-3.55 (m, 2H), 2.38-2.34 (m, 2H), 1.17 (d, J=6.4 Hz, 6H).

Step 5: Preparation of tert-butyl N-[(1S)-2-[[4-[6-[cis-2,6-dimethylmorpholin-4-yl]-2-pyridyl]thiazol-2-yl]amino]-1-(methoxymethyl)-2-oxo-ethyl]carbamate (Intermediate I)

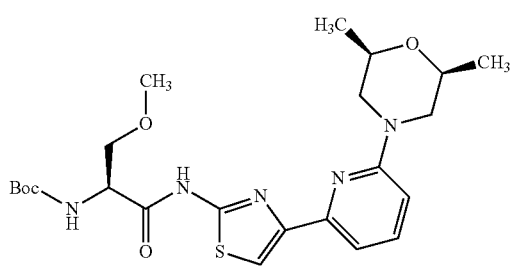

To a solution of Intermediate G (12.0 g, 41.3 mmol) and (2S)-2-(tertbutoxycarbonylamino)-3-methoxy-propanoic acid (10.9 g, 49.6 mmol) in dichloromethane (60 mL) was added EEDQ (12.3 g, 49.6 mmol). After stirring at room temperature for 16 h, the reaction mixture was concentrated under reduced pressure to give a residue. The residue was purified by silica gel column chromatography (petroleum ether:ethyl acetate=2:1 to 3:2) to give Intermediate 1 (20.0 g, 40.7 mmol, 98.5% yield) as a yellow gum.

LCMS (ESI) m/z: [M+H]$^+$=492.2.

$^1$H NMR (400 MHz, DMSO-d6) δ 12.37 (s, 1H), 7.78 (s, 1H), 7.64-7.60 (m, 1H), 7.25 (d, J=7.2 Hz, 1H), 7.16 (d, J=7.2 Hz, 1H), 6.79 (d, J=8.4 Hz, 1H), 4.50-4.48 (m, 1H), 4.25 (d, J=11.6 Hz, 2H), 3.70-3.51 (m, 4H), 3.26 (s, 3H), 2.44-2.40 (m, 2H), 1.39 (s, 9H), 1.18 (d, J=6.4 Hz, 6H).

Step 6: Preparation of (S)-4-(4-(6-(cis-2,6-dimethylmorpholino)pyridin-2-yl)thiazol-2-yl)-1-methoxy-3-oxobutan-2-aminium chloride (Intermediate J)

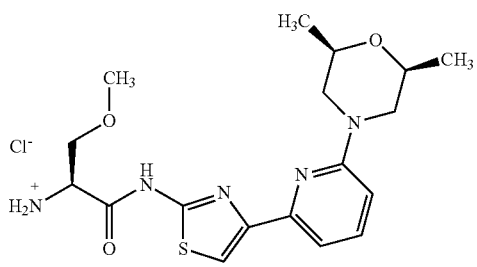

To a solution of 4M HCl in 1,4-dioxane (200 mL, 800 mmol) was added a solution of Intermediate I (20.0 g, 40.7 mmol) in dichloromethane (50 mL). After stirring at room temperature for 2 h, the mixture was diluted with methyl tert-butyl ether resulting in a suspension. The solid was collected by filtration, washed twice with methyl tert-butyl ether, and dried in vacuo to give Intermediate J (19.0 g) as a yellow solid, which was used in the next step without further purification.

LCMS (ESI) m/z: [M+H]$^+$=392.3.

$^1$H NMR (400 MHz, DMSO-d6) δ 13.44-12.30 (m, 1H), 8.65 (d, J=4.4 Hz, 3H), 7.87 (s, 1H), 7.66-7.64 (m, 1H), 7.25 (d, J=7.2 Hz, 1H), 6.83 (d, J=8.8 Hz, 1H), 4.39-4.30 (m, 1H), 4.25 (d, J=11.6 Hz, 2H), 3.94-3.86 (m, 1H), 3.85-3.77 (m, 1H), 3.69-3.57 (m, 2H), 3.31 (s, 3H), 2.43 (m, 2H), 1.18 (d, J=6.4 Hz, 6H).

Preparation of 1-(methylsulfonyl)-1H-pyrrole-3-carboxylic acid (Intermediate K)

1-(methylsulfonyl)-1H-pyrrole-3-carboxylic acid was synthesized as shown in Scheme 2 below.

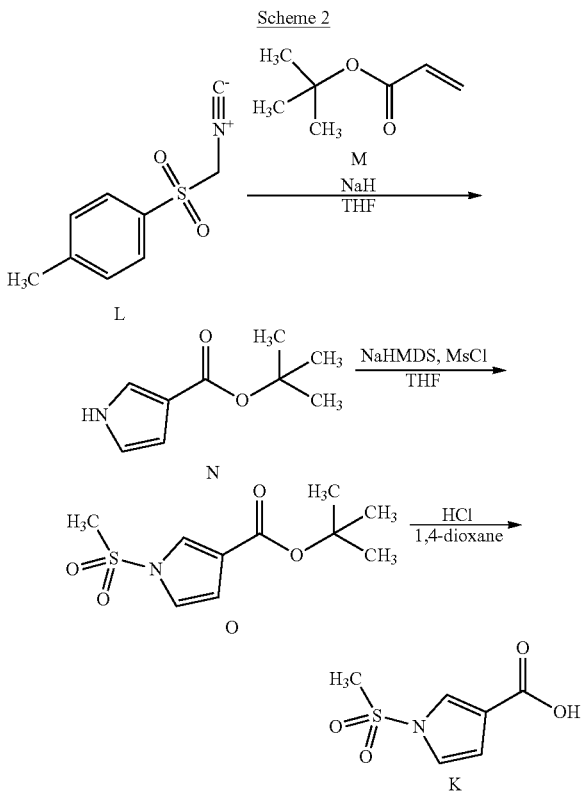

Scheme 2

Step A: Preparation of tert-butyl 1H-pyrrole-3-carboxylate (Intermediate N)

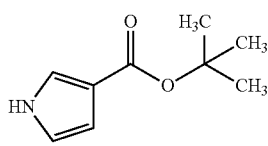

To a mixture of tert-butyl-prop-2-enoate (78.6 mL, 542 mmol) and 1-(isocyanomethylsulfonyl)-4-methylbenzene (106 g, 542 mmol) in THF (1300 mL) was added 60% NaH in mineral oil (25.97 g, 649 mmol) slowly at 30° C. over 1 hour and then heated to 70° C. After 2 h, the reaction mixture was poured into saturated aqueous NH$_4$Cl solution and extracted three times with ethyl acetate. The combined organic phase was washed twice with brine, dried over anhydrous Na$_2$SO$_4$, filtered, and concentrated under reduced pressure to afford a residue. The residue was purified by silica gel column chromatography (petroleum ether:ethyl acetate=20:1 to 3:1) to afford Intermediate N (41.5 g, 236 mmol, 43% yield) as a yellow solid.

LCMS (ESI) m/z [M+Na]⁺=180.4.

¹H NMR (400 MHz, CDCl₃) δ 8.36 (br s, 1H), 7.35-7.25 (m, 1H), 6.71-6.62 (m, 1H), 6.59-6.49 (m, 1H), 1.48 (s, 9H).

Step B: Preparation of tert-butyl 1-methylsulfonylpyrrole-3-carboxylate (Intermediate O)

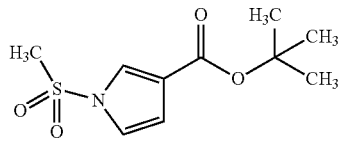

To a cooled solution (0° C.) of Intermediate N (40.5 g, 242 mmol) in THF (1500 mL) was added a 1M solution of NaHMDS (484 mL, 484 mmol). After stirring at 0° C. for 30 min, methanesulfonyl chloride (28.1 mL, 363 mmol) was slowly added and the mixture was warmed to 30° C. After 16 h, the reaction mixture was slowly poured into saturated aqueous NH₄Cl solution and extracted three times with ethyl acetate. The combined organic layers were washed twice with brine, dried over anhydrous Na₂SO₄, filtered, and concentrated under reduced pressure to afford a residue. The residue was purified by silica gel chromatography (petroleum ether:ethyl acetate=10:1) to afford a yellow solid. The yellow solid was triturated with methyl tert-butyl ether at room temperature, stirred for 20 minutes, filtered, and dried in vacuum to afford Intermediate O (25.7 g, 105 mmol, 43% yield) as a white solid.

¹H NMR (400 MHz, CDCl₃) δ 7.66-7.64 (m, 1H), 7.10-7.08 (m, 1H), 6.73-6.71 (m, 1H), 3.21 (s, 3H), 1.56 (s, 9H).

Step C: Preparation of 1-methylsulfonylpyrrole-3-carboxylic acid (Intermediate K)

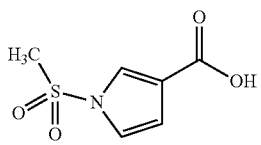

To a mixture of Intermediate O (25.7 g, 105 mmol) in 1,4-dioxane (100 mL) was added a 4M solution of HCl in 1,4-dioxane (400 mL, 1.6 mol) at 15° C. After stirring at at 15° C. for 14 h, the reaction mixture was concentrated under reduced pressure to afford a residue. The residue was triturated with methyl tert-butyl ether at 15° C. for 16 h. The mixture was filtered and dried in vacuum to afford Intermediate K (18.7 g, 98.8 mmol, 94% yield) as a white solid.

LCMS (ESI) m/z [M+H]⁺=189.8.

¹H NMR (400 MHz, methanol-d4) δ 7.78-7.77 (m, 1H), 7.25-7.23 (m, 1H), 6.72-6.70 (m, 1H), 3.37 (s, 3H).

Step 7: Preparation of N—((S)-1-((4-(6-(cis-2,6-dimethylmorpholino)pyridin-2-yl)thiazol-2-yl)amino)-3-methoxy-1-oxopropan-2-O-1-(methylsulfonyl)-1H-pyrrole-3-carboxamide

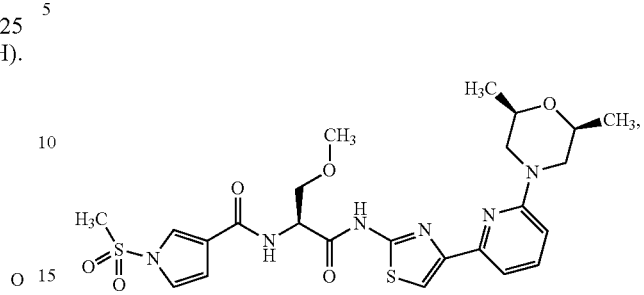

To a solution of 1-methylsulfonylpyrrole-3-carboxylic acid (Intermediate K) (2.43 g, 12.9 mmol), EDCI (2.69 g, 14.0 mmol), HOBt (1.89 g, 14.0 mmol), and DIPEA (10.2 mL, 58.4 mmol) in dichloromethane (50 mL) was added Intermediate J (5.00 g, 11.7 mmol). After stirring at room temperature for 4 h, the reaction mixture was concentrated under reduced pressure. The residue was diluted with water and extracted three times with ethyl acetate. The combined organic layers were washed three times with saturated aqueous NH₄Cl, once with brine, dried over Na₂SO₄, filtered, and concentrated under reduced pressure to give a residue. The residue was purified by silica gel column chromatography (petroleum ether:ethyl acetate=1:1 to 1:2). The residue was triturated with methyl tert-butyl ether. After 0.5 h, the suspension was filtered, the filter cake was washed with methyl tert-butyl ether, and dried in vacuo. The solid was dissolved in dimethyl sulfoxide (12 mL) and added dropwise to water (800 mL). The suspension was filtered to give wet filter cake. The filter cake was suspended in water and stirred at room temperature. After 1 hour, the solid was collected by filtration, washed three times with water and dried in vacuo to give N—((S)-1-((4-(6-(cis-2,6-dimethylmorpholino)pyridin-2-yl)thiazol-2-yl)amino)-3-methoxy-1-oxopropan-2-yl)-1-(methylsulfonyl)-1H-pyrrole-3-carboxamide (3.9 g, 6.93 mmol, 59.3% yield) as a white solid.

LCMS (ESI) m/z: [M+H]⁺=563.1.

¹H NMR (400 MHz, DMSO-d6) δ 12.49 (br s, 1H), 8.51 (d, J=7.2 Hz, 1H), 7.98-7.97 (m, 1H), 7.78 (s, 1H), 7.67-7.57 (m, 1H), 7.29-7.27 (m, 1H), 7.26 (d, J=7.2 Hz, 1H), 6.88-6.74 (m, 2H), 4.94-4.91 (m, 1H), 4.25 (d, J=11.6 Hz, 2H), 3.77-3.67 (m, 2H), 3.63-3.62 (m, 2H), 3.57 (s, 3H), 3.31 (s, 3H), 2.44-2.38 (m, 2H), 1.18 (d, J=6.0 Hz, 6H).

Example 2. Preparation of N—((S)-1-((4-(6-(cis-2,6-dimethylmorpholino)pyridin-2-yl)thiazol-2-yl)amino)-3-(methoxy-d₃)-1-oxopropan-2-yl-3,3-d₂)-1-(methylsulfonyl)-1H-pyrrole-3-carboxamide

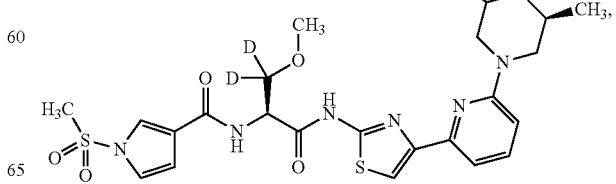

N—((S)-1-((4-(6-(cis-2,6-dimethylmorpholino)pyridin-2-yl)thiazol-2-yl)amino)-3-(methoxy-d3)-1-oxopropan-2-yl-3,3-d2)-1-(methylsulfonyl)-1H-pyrrole-3-carboxamide was prepared according to the synthetic protocol described in Example 1 with Intermediate H replaced with N-(tert-Butoxycarbonyl)-O-(methyl-d3)-L-serine-3,3-d2. N-(tert-Butoxycarbonyl)-O-(methyl-d3)-L-serine-3,3-d2 was prepared from isotopically enriched material according to synthetic procedures described in A. Yang et al, *Org. Process Res. Dev.* 2019, 23, 818-824.

LCMS (ESI) m/z: $[M+H]^+=568.2$.

$^1$H NMR (400 MHz, DMSO-d6) δ 12.45 (s, 1H), 8.47 (d, J=7.2 Hz, 1H), 7.98 (dd, J=2.3, 1.7 Hz, 1H), 7.78 (s, 1H), 7.62 (dd, J=8.5, 7.4 Hz, 1H), 7.29 (dd, J=3.2, 2.3 Hz, 1H), 7.26 (d, J=7.3 Hz, 1H), 6.84-6.75 (m, 2H), 4.91 (d, J=7.2 Hz, 1H), 4.25 (dd, J=13.1, 2.3 Hz, 2H), 3.69-3.59 (m, 2H), 3.56 (s, 3H), 2.42 (dd, J=12.8, 10.5 Hz, 2H), 1.18 (d, J=6.2 Hz, 6H).

Example 3. Preparation of N—((R)-1-((4-(6-(cis-2,6-dimethylmorpholino)pyridin-2-yl)thiazol-2-yl)amino)-3-(methoxy)-1-oxopropan-2-yl)-1-(methylsulfonyl)-1H-pyrrole-3-carboxamide N—((R)-1-((4-(6-(cis-2,6-dimethylmorpholino)pyridin-2-yl)thiazol-2-yl)amino)-3-(methoxy)-1-oxopropan-2-yl)-1-(methylsulfonyl)-1H-pyrrole-3-carboxamide was prepared according to the synthetic protocol described in Example 1 with Intermediate H replaced with (2R)-2-(tertbutoxycarbonylamino)-3-methoxy-propanoic acid.

LCMS (ESI) m/z: $[M+H]^+=563.1$.

$^1$H NMR (400 MHz, DMSO-d6) δ 12.5 (s, 1H), 8.50 (d, J=7.2 Hz, 1H), 7.98 (t, J=1.6 Hz, 1H), 7.78 (s, 1H), 7.62 (dd, J=7.2, 8.4 Hz, 1H), 7.29 (dd, J=2.0, 3.2 Hz, 1H), 7.26 (d, J=7.2 Hz, 1H), 6.79-6.81 (m, 2H), 4.92 (q, J=6.4, 12.8 Hz, 1H), 4.25 (d, J=11.2 Hz, 2H), 3.69-3.75 (m, 2H), 3.59-3.66 (m, 2H), 3.56 (s, 3H), 3.31 (s, 3H), 2.41 (dd, J=10.8, 12.8 Hz, 2H), 1.18 (d, J=6.0 Hz, 6H).

Example 4. Preparation of N—((R)-1-((4-(6-(cis-2,6-dimethylmorpholino)pyridin-2-yl)thiazol-2-yl)amino)-3-(methoxy-d$_3$)-1-oxopropan-2-yl-3,3-d$_2$)-1-(methylsulfonyl)-1H-pyrrole-3-carboxamide N—((R)-1-((4-(6-(cis-2,6-dimethylmorpholino)pyridin-2-yl)thiazol-2-yl)amino)-3-(methoxy-d3)-1-oxopropan-2-yl-3,3-d2)-1-(methylsulfonyl)-1H-pyrrole-3-carboxamide was prepared according to the synthetic protocol described in Example 1 with Intermediate H replaced with N-(tert-Butoxycarbonyl)-O-(methyl-d3)-D-serine-3,3-d2. N-(tert-Butoxycarbonyl)-O-(methyl-d3)-D-serine-3,3-d2 was prepared from isotopically enriched material according to synthetic procedures described in A. Yang et al, *Org. Process Res. Dev.* 2019, 23, 818-824.

LCMS (ESI) m/z: $[M+H]^+=568.3$.

$^1$H NMR (400 MHz, DMSO-d6) δ 12.46 (s, 1H), 8.52-8.38 (m, 1H), 7.97 (t, J=1.9 Hz, 1H), 7.76 (s, 1H), 7.62 (dd, J=8.5, 7.3 Hz, 1H), 7.29 (dd, J=3.3, 2.3 Hz, 1H), 7.26 (d, J=7.4 Hz, 1H), 6.79 (dt, J=5.1, 1.8 Hz, 2H), 4.89 (d, J=5.2 Hz, 1H), 4.31-4.20 (m, 2H), 3.63 (ddd, J=10.5, 6.2, 2.5 Hz, 2H), 3.56 (s, 3H), 2.41 (dd, J=12.8, 10.5 Hz, 2H), 1.18 (d, J=6.2 Hz, 6H).

Example 5. Assay for ATPase Catalytic Activity of BRM and BRG-1

The ATPase catalytic activity of BRM or BRG-1 was measured by an in vitro biochemical assay using ADP-Glo™ (Promega, V9102). The ADP-Glo™ kinase assay was performed in two steps once the reaction was complete. The first step is to deplete any unconsumed ATP in the reaction. The second step was to convert the reaction product ADP to ATP, which will be utilized by the luciferase to generate luminesce and be detected by a luminescence reader, such as Envision.

The assay reaction mixture (10 μL) contained 30 nM of BRM or BRG-1, 20 nM salmon sperm DNA (from Invitrogen, UltraPure™ Salmon Sperm DNA Solution, cat #15632011), and 400 μM of ATP in the ATPase assay buffer, which comprises of 20 mM Tris, pH 8, 20 mM MgCl$_2$, 50 mM NaCl, 0.1% Tween-20, and 1 mM fresh DTT (Pierce™ DTT (Dithiothreitol), cat #20290). The reaction was initiated by the addition of the 2.5 μL ATPase solution to 2.5 μL ATP/DNA solution on low volume white Proxiplate-384 plus plate (PerkinElmer, cat #6008280) and incubated at room temperature for 1 hour. Then following addition of 5 μL of ADP-Glo™ Reagent provided in the kit, the reaction incubated at room temperature for 40 minutes. Then 10 μL of Kinase Detection Reagent provided in the kit was added to convert ADP to ATP, and the reaction incubated at room temperature for 60 minutes. Finally, luminescence measurement is collected with a plate-reading luminometer, such as Envision.

BRM and BRG-1 were synthesized from high five insect cell lines with a purity of greater than 90%.

N—((S)-1-((4-(6-(cis-2,6-dimethylmorpholino)pyridin-2-yl)thiazol-2-yl)amino)-3-methoxy-1-oxopropan-2-yl)-1-(methylsulfonyl)-1H-pyrrole-3-carboxamide was found to have an IP$_{60}$ of 3.9 nM against BRM and 5.2 nM against BRG1 in the assay. N—((R)-1-((4-(6-(cis-2,6-dimethylmorpholino)pyridin-2-yl)thiazol-2-yl)amino)-3-(methoxy-d3)-1-oxopropan-2-yl-3,3-d2)-1-(methylsulfonyl)-1H-pyrrole-3-carboxamide was found to have an IP$_{60}$ of 443 nM against BRM and 777 nM against BRG1 in the assay. N—((S)-1-((4-(6-(cis-2,6-dimethylmorpholino)pyridin-2-yl)thiazol-2-yl)amino)-3-(methoxy-d3)-1-oxopropan-2-yl-3,3-d2)-1-(methylsulfonyl)-1H-pyrrole-3-carboxamide was found to have an IP$_{60}$ of 4.6 nM against BRM and 7.4 nM against BRG1 in the assay.

Example 6. Synthesis of Compound A

BRG1/BRM Inhibitor Compound A has the structure:

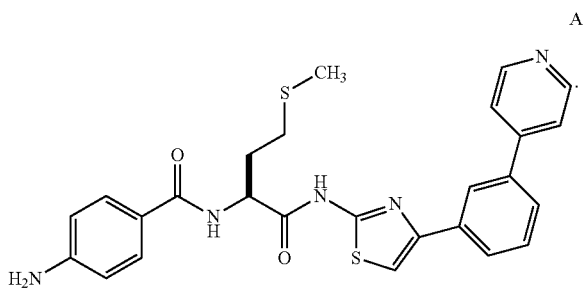 [SMILES: CSCC[C@H](NC(=O)c1ccc(N)cc1)C(=O)Nc1nc(-c2cccc(-c3ccncc3)c2)cs1]

Compound A was synthesized as shown in Scheme 3 below.

Scheme 3. Synthesis of Compound A

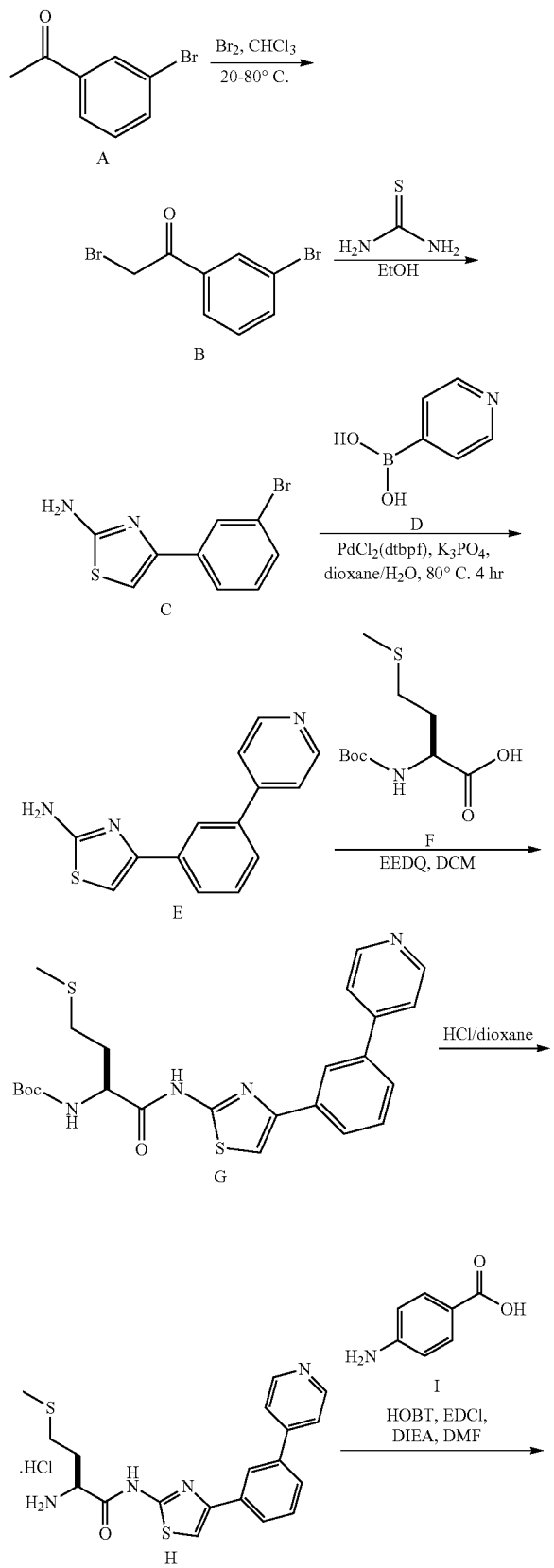

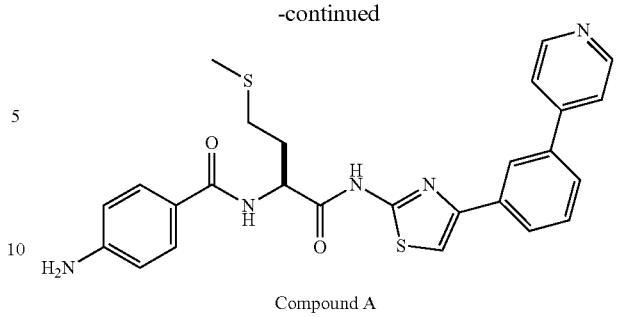

Compound A

The ATPase catalytic activity of BRM or BRG-1 in the presence of Compound A was measured by the in vitro biochemical assay using ADP-Glo™ (Promega, V9102) described above. Compound A was found to have an IP50 of 10.4 nM against BRM and 19.3 nM against BRG1 in the assay.

Example 7. Effects of BRG1/BRM ATPase Inhibition on the Growth of Uveal Melanoma and Hematological Cancer Cell Lines Procedure: Uveal melanoma cell lines (92-1, MP41, MP38, MP46), prostate cancer cell lines (LNCAP), lung cancer cell lines (NCI-H1299), and immortalized embryonic kidney lines (HEK293T) were plated into 96 well plates with growth media (see Table 1). BRG1/BRM ATPase inhibitor, Compound A, was dissolved in DMSO and added to the cells in a concentration gradient from 0 to 10 μM at the time of plating. Cells were incubated at 37° C. for 3 days. After three days of treatment, the media was removed from the cells, and 30 microliters of TrypLE (Gibco) was added to cells for 10 minutes. Cells were detached from the plates, and resuspended with the addition of 170 microliters of growth media. Cells from two DMSO-treated control wells were counted, and the initial number of cells plated at the start of the experiment, were re-plated into fresh-compound containing plates for an additional four days at 37° C. At day 7, cells were harvested as described above. On day 3 and day 7, relative cell growth was measured by the addition of Cell-titer glo (Promega), and luminescence was measured on an Envision plate reader (Perkin Elmer). The concentration of compound at which each cell line's growth was inhibited by 50% ($GI_{50}$), was calculated using Graphpad Prism, and is plotted below. For multiple myeloma cell lines (OPM2, MM1S, LP1), ALL cell lines (TALL1, JURKAT, RS411), DLBCL cell lines (SUDHL6, SUDHL4, DB, WSUDLCL2, PFEIFFER), AML cell lines (OCIAML5), MDS cell lines (SKM1), ovarian cancer cell lines (0V7, TYKNU), esophageal cancer cell lines (KYSE150), rhabdoid tumor lines (RD, G402, G401, HS729, A204), liver cancer cell lines (HLF, HLE, PLCRPFS), and lung cancer cell lines (SW1573, NCIH2444), the above methods were performed with the following modifications: Cells were plated in 96 well plates, and the next day, BRG1/BRM ATPase inhibitor, Compound A, was dissolved in DMSO and added to the cells in a concentration gradient from 0 to 10 μM. At the time of cell splitting on days 3 and 7, cells were split into new 96 well plates, and fresh compound was added four hours after re-plating. Table 1 lists the tested cell lines and growth media used.

TABLE 1

| Cell Lines and Growth Media | | |
|---|---|---|
| Cell Line | Source | Growth Media |
| 92-1 | SIGMA | RPMI1640 + 20% FBS |
| A204 | ATCC | McCoy's 5A + 10% FBS |
| DB | ATCC | RPMI1640 + 10% FBS |
| G401 | ATCC | McCoy's 5A + 10% FBS |
| G402 | ATCC | McCoy's 5A + 10% FBS |
| HEK293T | ATCC | DMEM + 10% FBS |
| HLE | JCRB | DMEM + 10% FBS |
| HLF | JCRB | DMEM + 10% FBS |
| H5729 | ATCC | DMEM + 10% FBS |
| JURKAT | ATCC | RPMI1640 + 10% FBS |
| KYSE150 | DSMZ | RPMI1640/Ham's F12 + 10% FBS |
| LNCAP | ATCC | RPMI1640 + 10% FBS |
| LP1 | DSMZ | IMDM + 20% FBS |
| MM1S | ATCC | RPMI1640 + 10% FBS |
| MP38 | ATCC | RPMI1640 + 20% FBS |
| MP41 | ATCC | RPMI1640 + 20% FBS |
| MP46 | ATCC | RPMI1640 + 20% FBS |
| NCIH1299 | ATCC | RPMI1640 + 10% FBS |
| NCIH2444 | ATCC | RPMI1640 + 20% FBS |
| OCIAML5 | DSMZ | alpha-MEM + 20% FBS + 10 ng/ml GM-CSF |
| OPM2 | DSMZ | RPMI1640 + 10% FBS |
| OV7 | ECACC | DMEM/Ham's F12 (1:1) + 2 mM Glutamine + 10% FBS + 0.5 ug/ml hydrocortisone + 10 ug/ml insulin |
| PFEIFFER | ATCC | RPMI1640 + 10% FBS |
| PLCPRF5 | ATCC | EMEM + 10% FBS |
| RD | ATCC | DMEM + 10% FBS |
| RS411 | ATCC | RPMI1640 + 10% FBS |
| SKM1 | JCRB | RPMI1640 + 10% FBS |
| SUDHL4 | DSMZ | RPMI1640 + 10% FBS |
| SUDHL6 | ATCC | RPMI1640 + 20% FBS |
| SW1573 | ATCC | DMEM + 10% FBS |
| TALL1 | JCRB | RPMI1640 + 10% FBS |
| TYKNU | JCRB | EMEM + 20% FBS |
| WSUDLCL2 | DSMZ | RPMI1640 + 10% FBS |

Results: As shown in FIG. 1, the uveal melanoma and hematologic cancer cell lines were more sensitive to BRG1/BRM inhibition than the other tested cell lines. Inhibition of the uveal melanoma and hematologic cancer cell lines was maintained through day 7.

Example 8. Comparison of BRG1/BRM Inhibitors to Clinical PKC and MEK Inhibitors in Uveal Melanoma Cell Lines Procedure: Uveal melanoma cell lines, 92-1 or MP41, were plated in 96 well plates in the presence of growth media (see Table 1). BAF ATPase inhibitors (Compound A), PKC inhibitor (LXS196; Med Chem Express), or MEK inhibitor (Selumetinib; Selleck Chemicals) were dissolved in DMSO and added to the cells in a concentration gradient from 0 to 10 µM at the time of plating. Cells were incubated at 37° C. for 3 days. After three days of treatment, cell growth was measured with Cell-titer glow (Promega), and luminescence was read on an Envision plate reader (Perkin Elmer).

Figure 2:
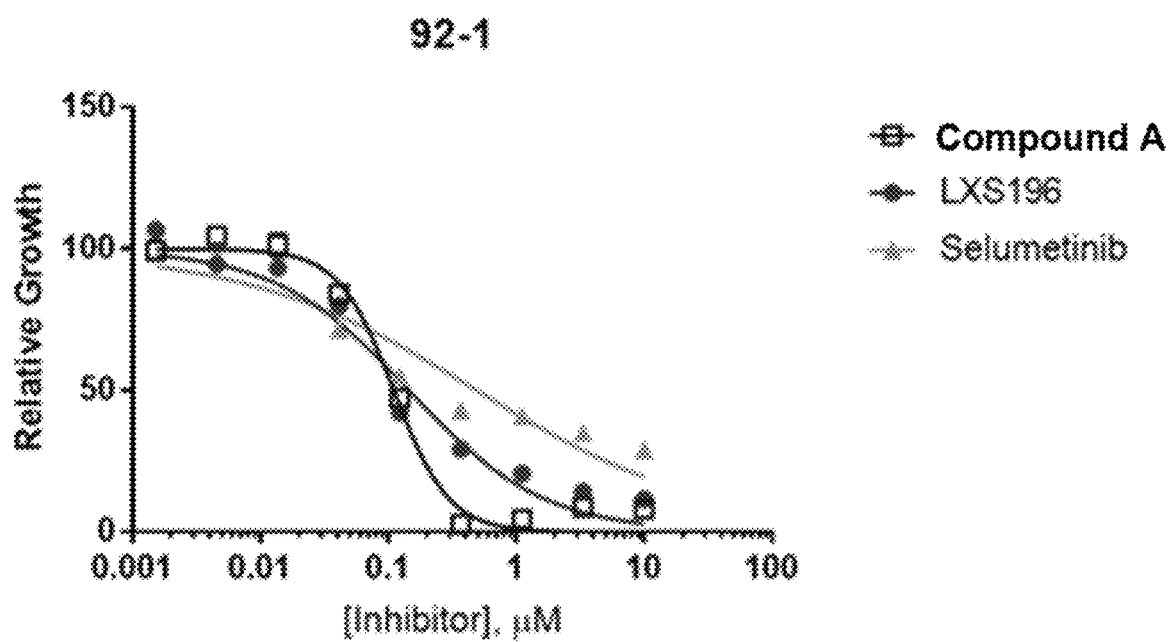
FIG. 2 is a graph illustrating inhibition of cell proliferation of uveal melanoma cell line 92-1 by a BRG1/BRM inhibitor (Compound A), a MEK inhibitor (Selumetinib), and a PKC inhibitor (LXS196).
Figure 3:
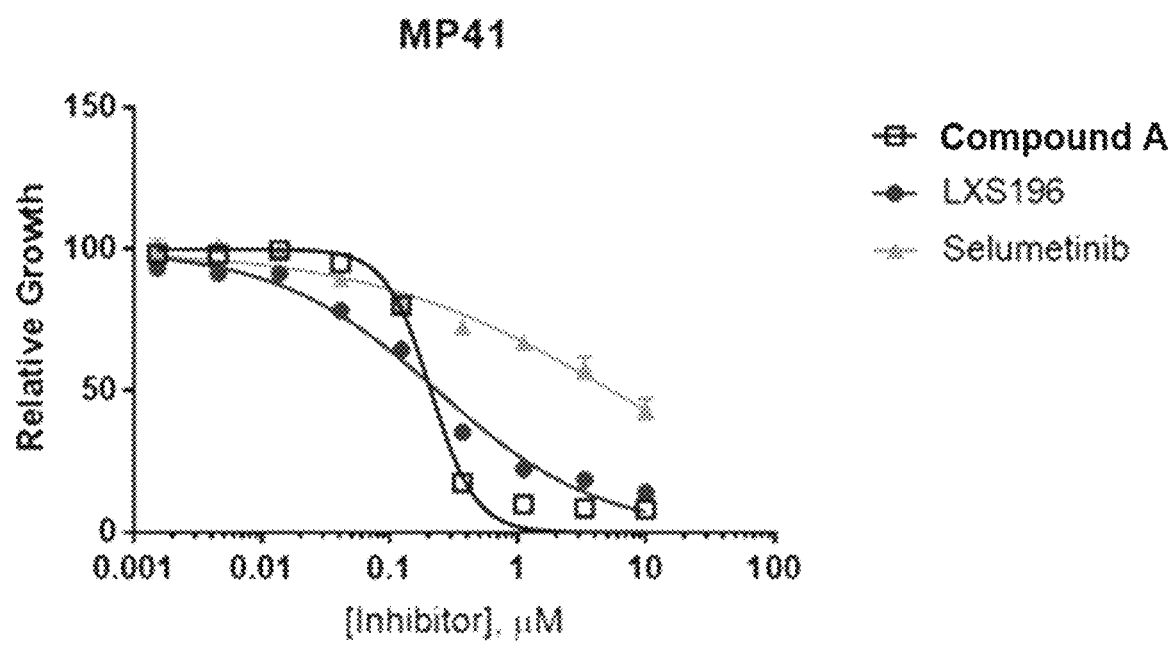
FIG. 3 is a graph illustrating inhibition of cell proliferation of uveal melanoma cell line MP41 by a BRG1/BRM inhibitor (Compound A), a MEK inhibitor (Selumetinib), and a PKC inhibitor (LXS196).

Results: As shown in FIG. 2 and FIG. 3, Compound A showed comparable growth inhibition of uveal melanoma cells as the clinical PKC and MEK inhibitors. Further, Compound A was found to result in a faster onset of inhibition than the clinical PKC and MEK inhibitors.

Example 9. Synthesis of Compound B

BRG1/BRM Inhibitor Compound B has the structure:

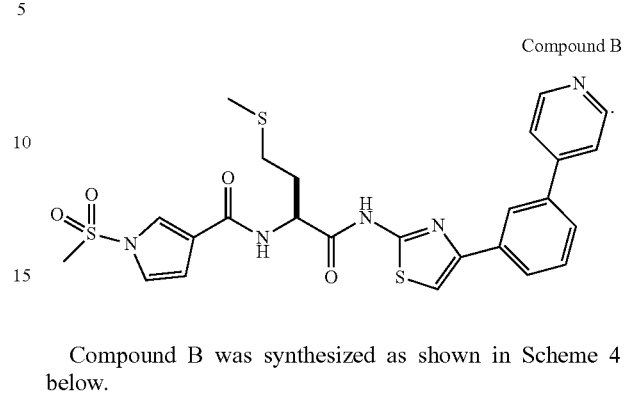

Compound B

Compound B was synthesized as shown in Scheme 4 below.

Scheme 4. Synthesis of Compound B

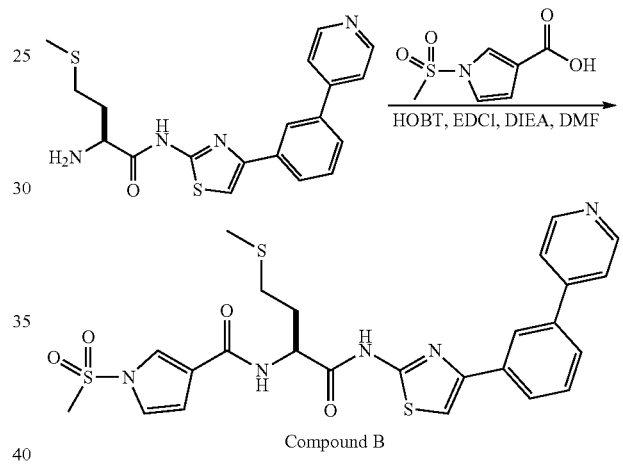

Compound B

To a mixture of (2S)-2-amino-4-methylsulfanyl-N-[4-[3-(4-pyridyl)phenyl]thiazol-2-yl]butanamide (2 g, 4.75 mmol, HCl salt) and 1-methylsulfonylpyrrole-3-carboxylic acid (898.81 mg, 4.75 mmol) in DMF (20 mL) was added EDCl (1.37 g, 7.13 mmol), HOBt (962.92 mg, 7.13 mmol), and DIEA (2.46 g, 19.00 mmol, 3.31 mL) and the mixture was stirred at 25° C. for 3 h. The mixture was poured into H$_2$O (100 mL) and the precipitate was collected by filtration. The solid was triturated in MeOH (20 mL) and the precipitate was collected by filtration. The solid was dissolved in DMSO (10 mL) and then the mixture was poured into MeOH (50 mL), and the formed precipitate was collected by filtration and lyophilized to give Compound B (2.05 g, 3.66 mmol, 77.01% yield) as a white solid.

LCMS (ESI) m/z [M+H]$^+$=555.9.

$^1$H NMR (400 MHz, DMSO) δ 12.49 (s, 1H), 8.68-8.66 (m, 2H), 8.46 (d, J=7.2 Hz, 1H), 8.31-8.30 (m, 1H), 8.02-8.00 (m, 1H), 7.94-7.96 (m, 1H), 7.83 (s, 1H), 7.73-7.74 (m, 3H), 7.61-7.57 (m, 1H), 7.31-7.29 (m, 1H), 6.79-6.77 (m, 1H), 4.74-4.69 (m, 1H), 3.57 (s, 3H), 2.67-2.53 (m, 2H), 2.13-2.01 (m, 5H). ee %=100%.

Compound B was found to have an IP$_{50}$ of 3.6 nM against BRM and 5.7 nM against BRG1 in the ATPase assay described.

Example 10. Effects of BRG1/BRM ATPase Inhibition on the Growth of Uveal Melanoma, Hematological Cancer, Prostate Cancer, Breast Cancer, and Ewing's Sarcoma Cell Lines Procedure: All cell lines described above in Example 7 were also tested as described above with Compound B. In addition, the following cell lines were also tested as follows. Briefly, for Ewing's sarcoma cell lines (CADOES1, RDES, SKES1), retinoblastoma cell lines (WERIRB1), ALL cell lines (REH), AML cell lines (KASUMI1), prostate cancer cell lines (PC3, DU145, 22RV1), melanoma cell lines (SH4, SKMEL28, WM115, COL0829, SKMEL3, A375), breast cancer cell lines (MDAMB415, CAMA1, MCF7, BT474, HCC1419, DU4475, BT549), B-ALL cell lines (SUPB15), CML cell lines (K562, MEG01), Burkitt's lymphoma cell lines (RAMOS2G64C10, DAUDI), mantle cell lymphoma cell lines (JEKO1, REC1), bladder cancer cell lines (HT1197), and lung cancer cell lines (SBC5), the above methods were performed with the following modifications: Cells were plated in 96 well plates, and the next day, BRG1/BRM ATPase inhibitor, Compound B, was dissolved in DMSO and added to the cells in a concentration gradient from 0 to 10 µM. At the time of cell splitting on days 3 and 7, cells were split into new 96 well plates, and fresh compound was added four hours after re-plating. Table 2 lists the tested cell lines and growth media used.

TABLE 2

Cell Lines And Growth Media

| Cell Line | Source | Growth Media |
|---|---|---|
| 22RV1 | ATCC | RPMI1640 + 10% FBS |
| A375 | ATCC | DMEM + 10% FBS |
| BT474 | ATCC | Hybricare medium + 1.5 g/L sodium bicarbonate + 10% FBS |
| BT549 | ATCC | RPMI1640 + 0.023 IU/ml insulin + 10% FBS |
| CADOES1 | DSMZ | RPMI1640 + 10% FBS |
| CAMA1 | ATCC | EMEM + 10% FBS |
| COL0829 | ATCC | RPMI1640 + 10% FBS |
| DAUDI | ATCC | RPMI1640 + 10% FBS |
| DU145 | ATCC | EMEM + 10% FBS |
| DU4475 | ATCC | RPMI1640 + 10% FBS |
| HCC1419 | ATCC | RPMI1640 + 10% FBS |
| HT1197 | ATCC | EMEM + 10% FBS |
| JEKO1 | ATCC | RPMI1640 + 20% FBS |
| K562 | ATCC | IMDM + 10% FBS |
| KASUMI1 | ATCC | RPMI1640 + 10% FBS |
| MCF7 | ATCC | EMEM + 0.01 mg/ml bovine insulin + 10% FBS |
| MDAM B415 | ATCC | Leibovitz's L-15 + 2 mM L-glutamine + 10 mcg/ml insulin + 10 mcg/ml glutathione + 15% FBS |
| MEG01 | ATCC | RPMI1640 + 10% FBS |
| PC3 | ATCC | F-12K + 10% FBS |
| RAMOS2G64C10 | ATCC | RPMI1640 + 10% FBS |
| RDES | ATCC | RPMI1640 + 15% FBS |
| REC1 | ATCC | RPMI1640 + 10% FBS |
| REH | ATCC | RPMI1640 + 10% FBS |
| SBC5 | JCRB | EMEM + 10% FBS |
| SH4 | ATCC | DMEM + 10% FBS |
| SKES1 | ATCC | McCoy's 5A + 15% FBS |
| SKMEL28 | ATCC | EMEM + 10% FBS |
| SKMEL3 | ATCC | McCoy's 5A + 15% FBS |
| SUPB15 | ATCC | IMDM + 4 mM L-glutamine + 1.5 g/L sodium bicarbonate + 0.05 mM 2-mercaptoethanol + 20% FBS |
| WERIRB1 | ATCC | RPMI1640 + 10% FBS |
| WM115 | ATCC | EMEM + 10% FBS |

Figure 4:
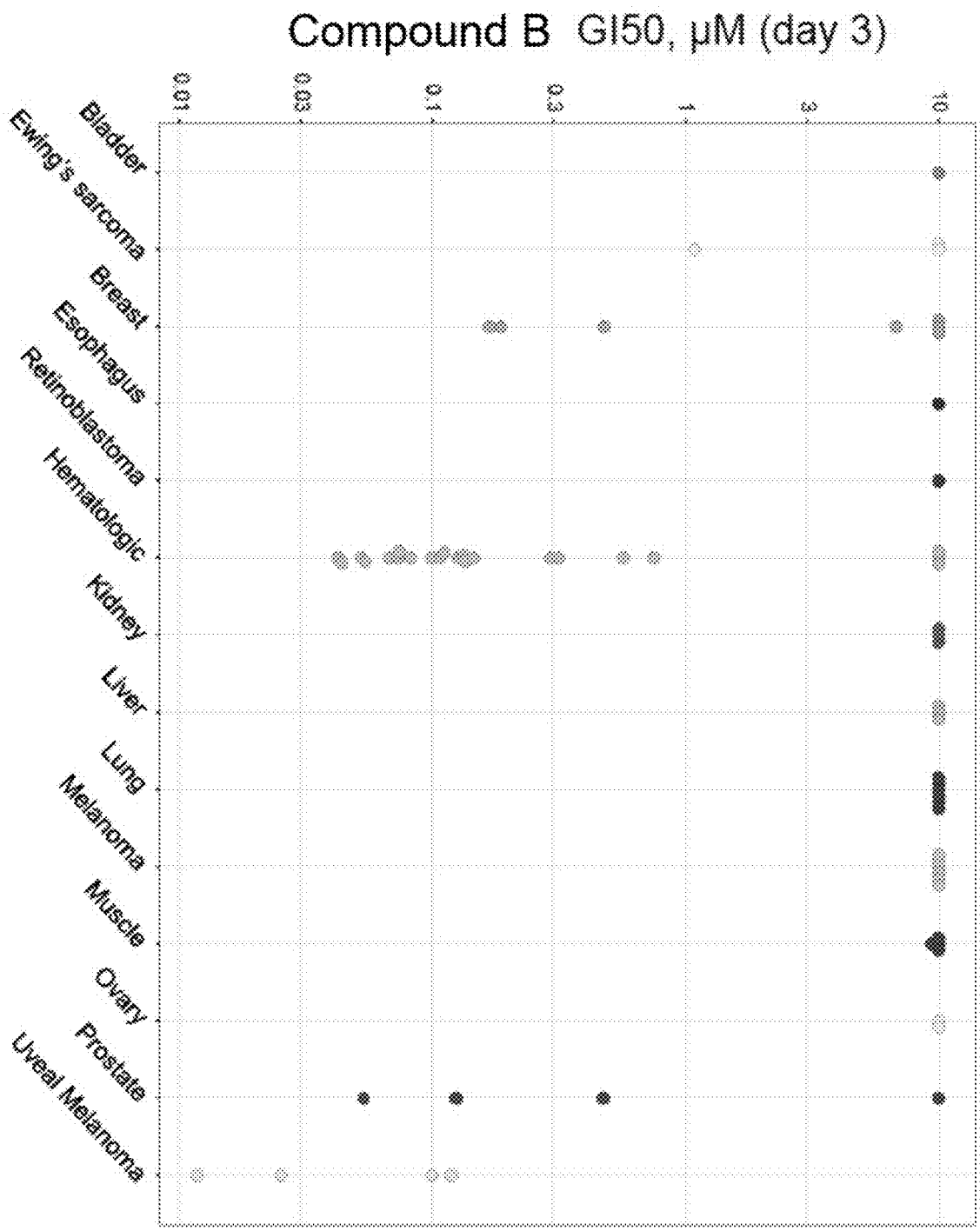
FIG. 4 is a graph illustrating inhibition of cell proliferation of several cancer cell lines by a BRG1/BRM inhibitor (Compound B).

Results: As shown in FIG. 4, the uveal melanoma, hematologic cancer, prostate cancer, breast cancer, and Ewing's sarcoma cell lines were more sensitive to BRG1/BRM inhibition than the other tested cell lines. Inhibition of the uveal melanoma, hematologic cancer, prostate cancer, breast cancer, and Ewing's sarcoma cell lines was maintained through day 7.

Example 11. Effects of BRG1/BRM ATPase Inhibition on the Growth of Cancer Cell Lines Procedure: A pooled cell viability assay was performed using PRISM (Profiling Relative Inhibition Simultaneously in Mixtures) as previously described ("High-throughput identification of genotype-specific cancer vulnerabilities in mixtures of barcoded tumor cell lines", Yu et al, Nature Biotechnology 34, 419-423, 2016), with the following modifications. Cell lines were obtained from the Cancer Cell Line Encyclopedia (CCLE) collection and adapted to RPMI-1640 medium without phenol red, supplemented with 10% heat-inactivated fetal bovine serum (FBS), in order to apply a unique infection and pooling protocol to such a big compendium of cell lines. A lentiviral spin-infection protocol was executed to introduce a 24 nucleotide-barcode in each cell line, with an estimated multiplicity of infection (MOI) of 1 for all cell lines, using blasticidin as selection marker. Over 750 PRISM cancer cell lines stably barcoded were then pooled together according to doubling time in pools of 25. For the screen execution, instead of plating a pool of 25 cell lines in each well as previously described (Yu et al.), all the adherent or all the suspension cell line pools were plated together using T25 flasks (100,000 cells/flask) or 6-well plates (50,000 cells/well), respectively. Cells were treated with either DMSO or compound in a 8-point 3-fold dose response in triplicate, starting from a top concentration of 10 µM. As control for assay robustness, cells were treated in parallel with two previously validated compounds, the pan-Raf inhibitor AZ-628, and the proteasome inhibitor bortezomib, using a top concentration of 2.5 µM and 0.039 µM, respectively.

Figure 5:
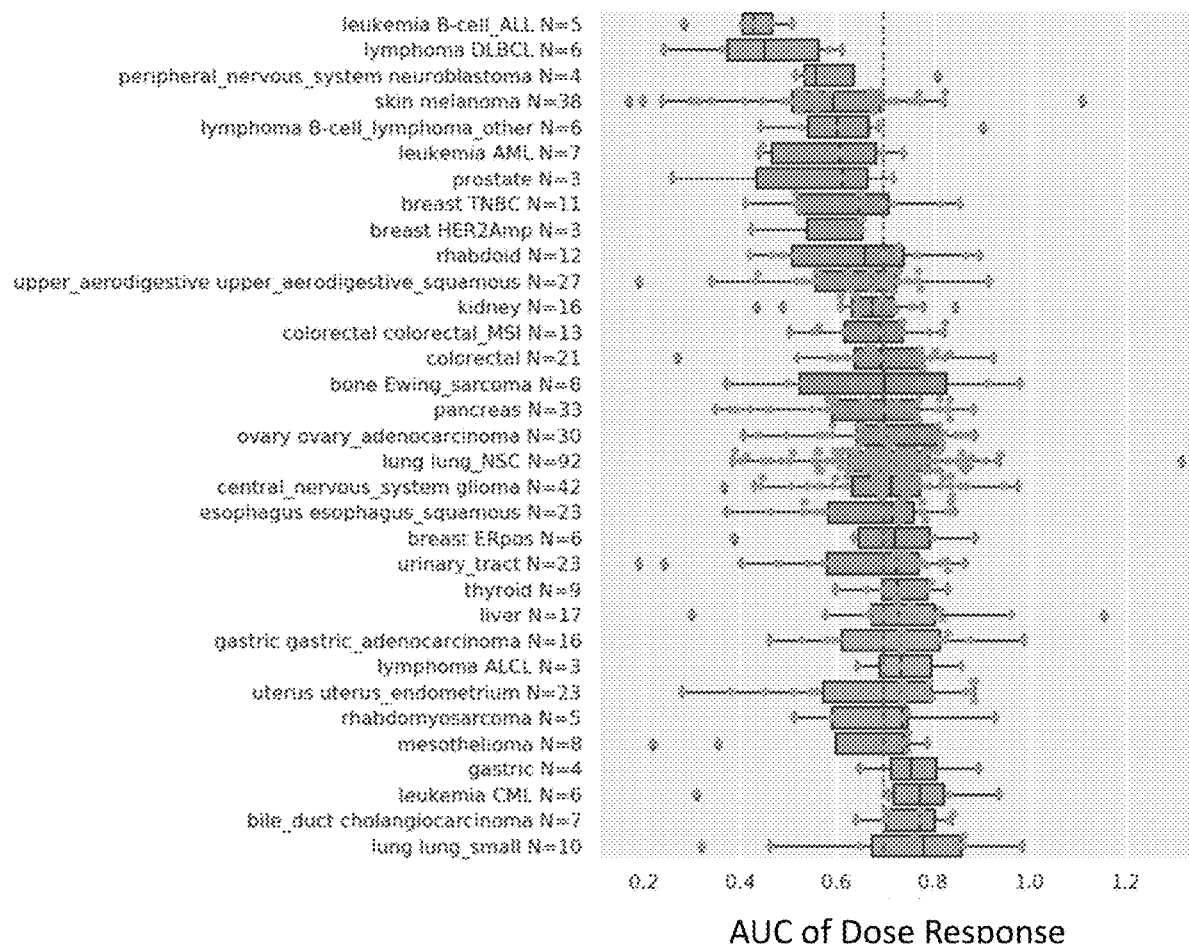
FIG. 5 is a graph illustrating the area under the curves (AUCs) calculated from dose-response curves for cancer cell lines treated with a BRG1/BRM inhibitor (Compound B).

Following 3 days of treatment with compounds, cells were lysed, genomic DNA was extracted, barcodes were amplified by PCR and detected with Next-Generation Sequencing. Cell viability was determined by comparing the counts of cell-line specific barcodes in treated samples to those in the DMSO-control and Day 0 control. Dose-response curves were fit for each cell line and corresponding area under the curves (AUCs) were calculated and compared to the median AUC of all cell lines (FIG. 5).

Results: Cell lines with AUCs less than the median were considered most sensitive.

Example 12. Effects of BRG1/BRM ATPase Inhibitors on the Growth of Uveal Melanoma Cell Lines Procedure: Uveal melanoma cell lines (92-1, MP41, MP38, MP46) and non-small cell lung cancer cells (NCIH1299) were plated into 96 well plates with growth media (see Table 2). BRG1/BRM ATPase inhibitor, Compound B, was dissolved in DMSO and added to the cells in a concentration gradient from 0 to 10 µM at the time of plating. Cells were incubated at 37° C. for 3 days. After three days of treatment, cell growth was measured with Cell-titer glow (Promega), and luminescence was read on an Envision plate reader (Perkin Elmer).

Figure 6:
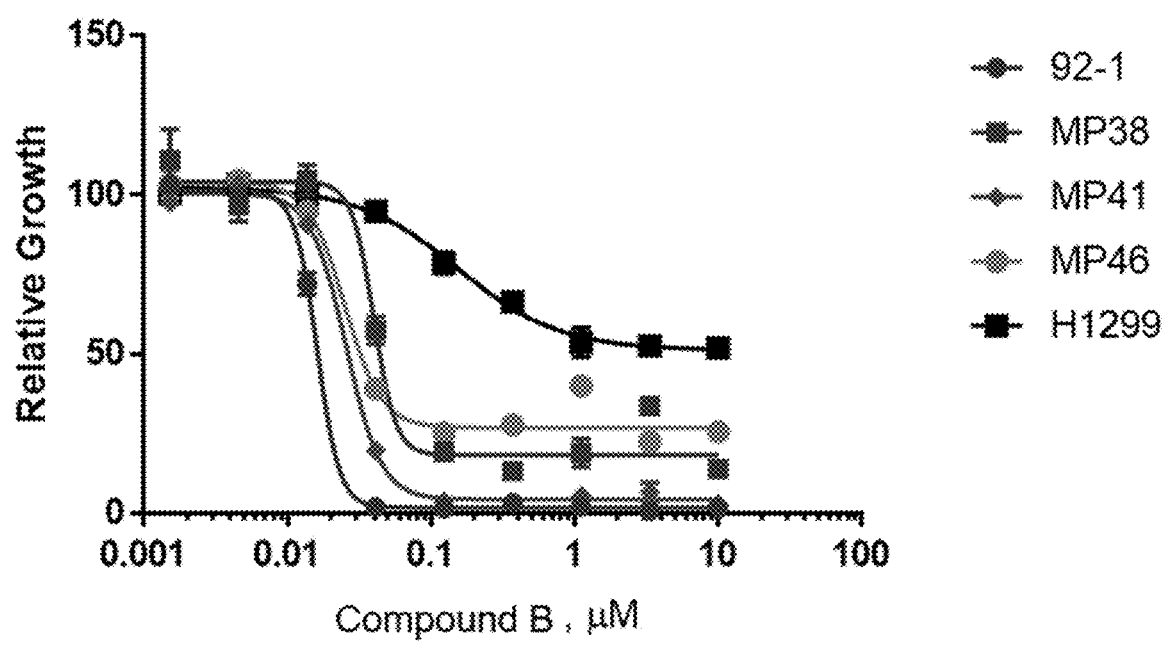
FIG. 6 is a graph illustrating inhibition of cell proliferation of uveal melanoma and non-small cell lung cancer cell lines by a BRG1/BRM inhibitor (Compound B).

Results: As shown in FIG. 6, Compound B resulted in potent growth inhibition in the cell lines.

Example 13. Comparison of BRG1/BRM Inhibitors to Clinical PKC and MEK Inhibitors in Uveal Melanoma Cell Lines Procedure: Uveal melanoma cell lines, 92-1 or MP41, were plated in 96 well plates in the presence of growth media (see Table 2). BAF ATPase inhibitor (Compound B), PKC inhibitor (LXS196; Med Chem Express), and MEK inhibitor (Selumetinib; Selleck Chemicals) were dissolved in DMSO and added to the cells in a concentration gradient from 0 to 10 µM at the time of plating. Cells were incubated at 37° C. for 3 days. After three days of treatment, cell growth was measured with Cell-titer glow (Promega), and luminescence was read on an Envision plate reader (Perkin Elmer).

Figure 7:
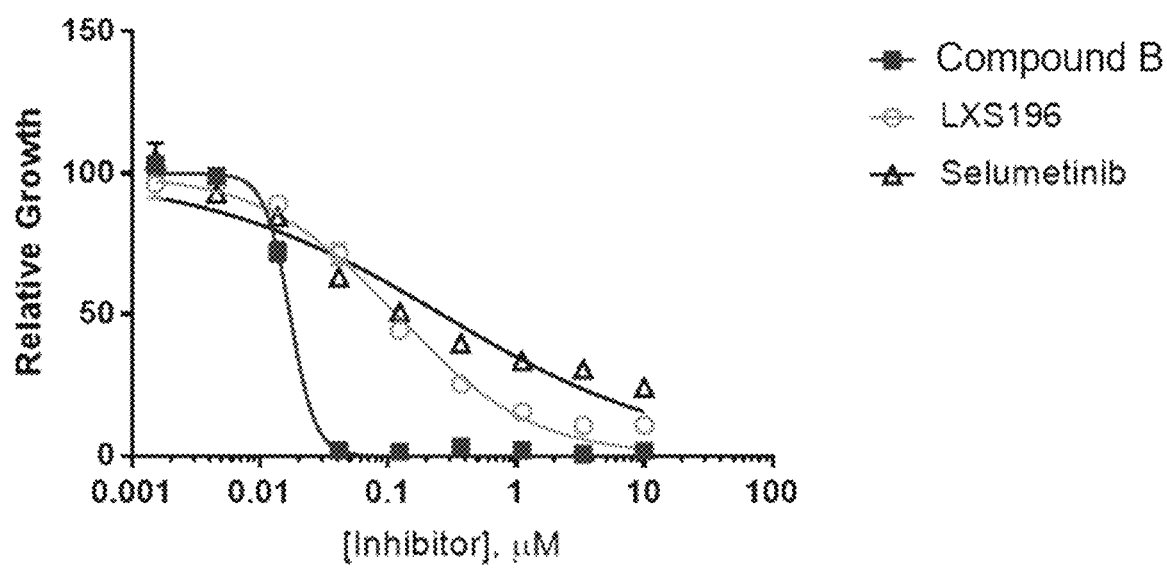
FIG. 7 is a graph illustrating inhibition of cell proliferation of uveal melanoma cell line 92-1 by a BRG1/BRM inhibitor (Compound B), a MEK inhibitor (Selumetinib), and a PKC inhibitor (LXS196).
Figure 8:
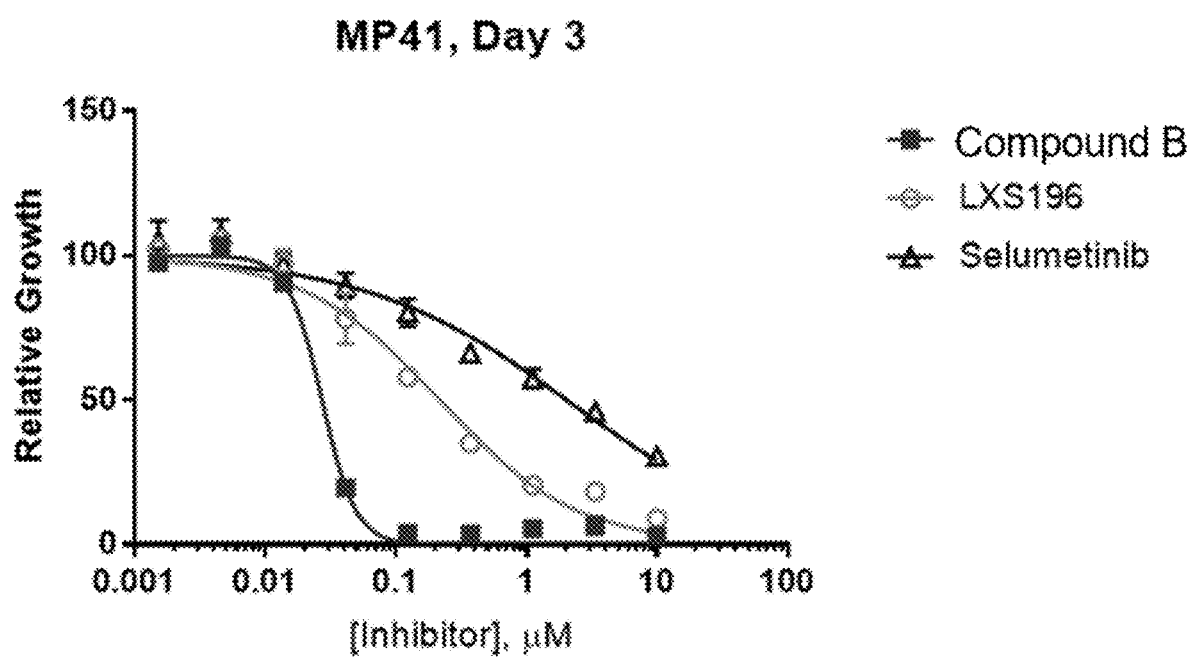
FIG. 8 is a graph illustrating inhibition of cell proliferation of uveal melanoma cell line MP41 by a BRG1/BRM inhibitor (Compound B), a MEK inhibitor (Selumetinib), and a PKC inhibitor (LXS196).

Results: As shown in FIG. 7 and FIG. 8, Compound B showed more potent effects on growth inhibition of uveal melanoma cells as compared to the clinical PKC and MEK inhibitors. Further, Compound B was found to result in a faster onset of growth inhibition than the clinical PKC and MEK inhibitors.

Example 14. BRG1/BRM ATPase Inhibitors are Effective at Inhibiting the Growth of PKC Inhibitor-Resistant Cells Procedure: MP41 uveal melanoma cells were made resistant to the PKC inhibitor (LXS196; Med Chem Express), by long-term culture in growth media (see Table 2) containing increasing concentrations of the compound, up to 1 µM. After 3 months, sensitivity of the parental MP41 cells and the PKC inhibitor (PKCi)-resistant cells to the PKC inhibitor (LXS196) or the BRG1/BRM ATPase inhibitor (Compound B) was tested in a 7-day growth inhibition assay as described above in Example 6.

Figure 9:
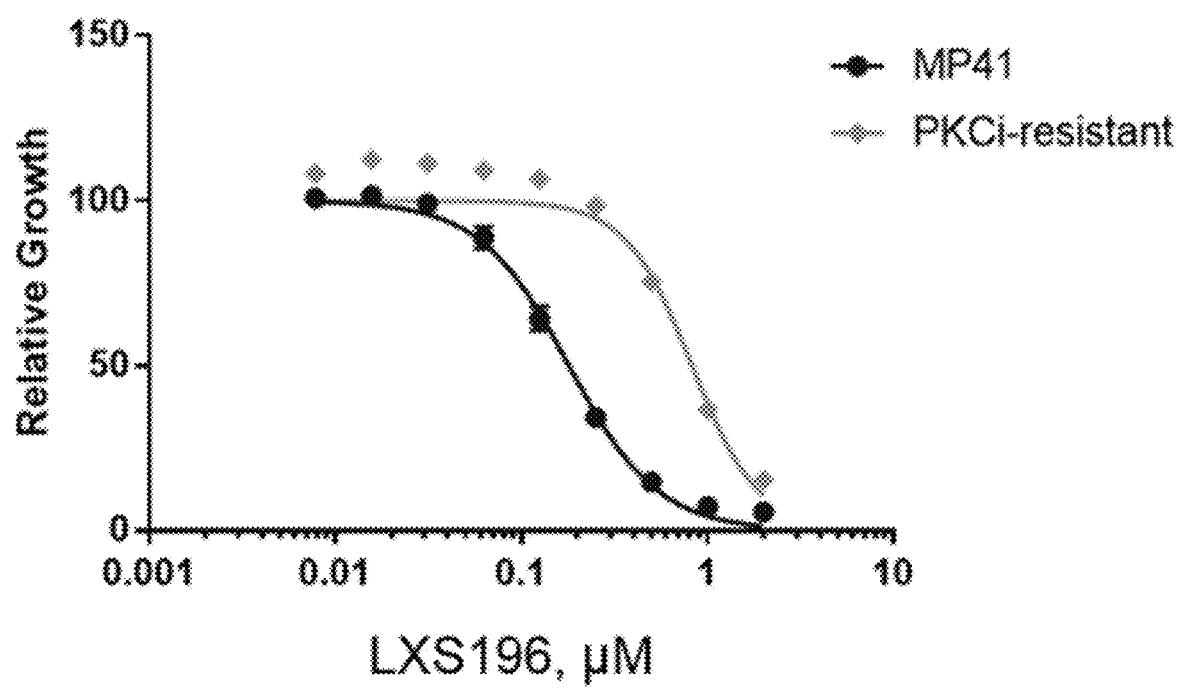
FIG. 9 is a graph illustrating inhibition of cell proliferation of parental and PKC-inhibitor refractory uveal melanoma cell lines by a PKC inhibitor (LXS196).
Figure 10:
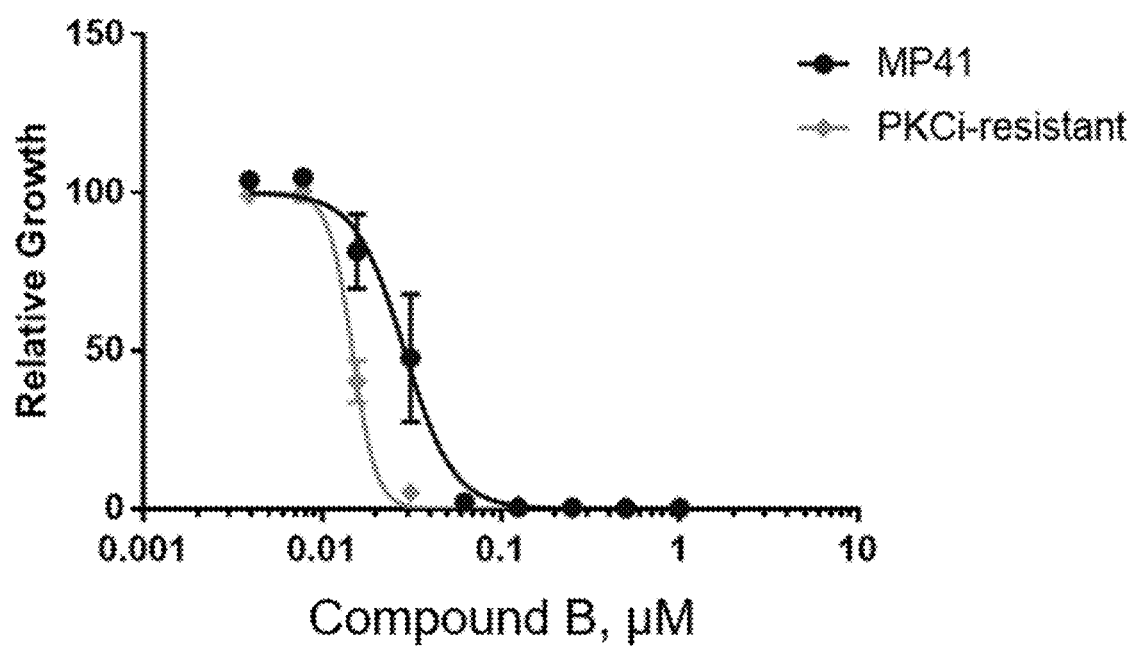
FIG. 10 is a graph illustrating inhibition of cell proliferation of parental and PKC-inhibitor refractory uveal melanoma cell lines by a BRG1/BRM inhibitor (Compound B).

Results: While the PKCi-resistant cells could tolerate growth at higher concentrations of LXS196 than could the parental MP41 cell line (FIG. 9), the BRG1/BRM ATPase inhibitor (Compound B) resulted in strong growth inhibition of both the PKCi-resistant and parental cell lines (FIG. 10). The PKCi-resistant cells were more sensitive to Compound B than were the parental MP41 cells (FIG. 10).

Example 15. Synthesis of Compound C

BRG1/BRM Inhibitor Compound C has the structure:

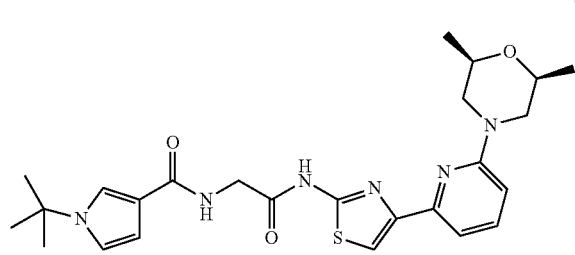

Compound C was synthesized as shown in Scheme 5 below.

Scheme 5. Synthesis of Compound C

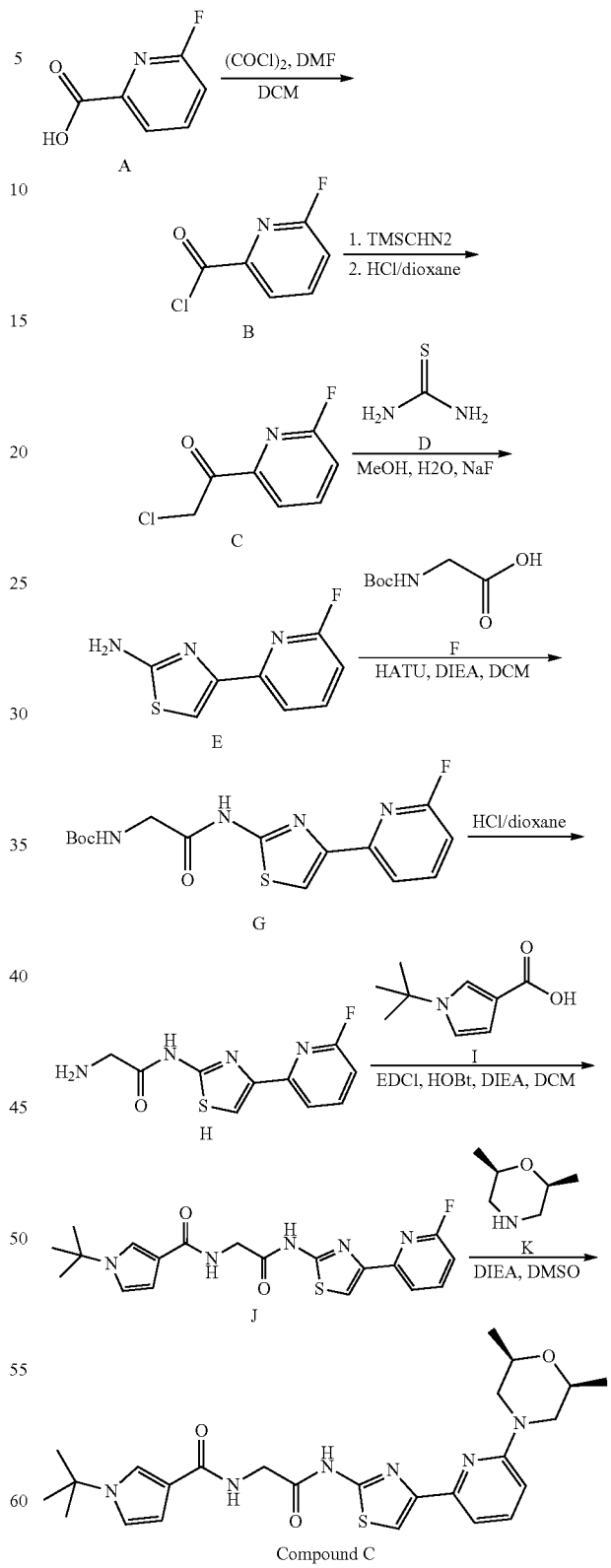

Compound C was found to have an $IP_{50}$ of 5.3 nM against BRM and 1.3 nM against BRG1 in the ATPase assay described above.

Example 16. BRG1/BRM ATPase Inhibitors Cause Uveal Melanoma Tumor Growth Inhibition In Vivo Procedure: Nude mice (Envigo) were engrafted subcutaneously in the axillary region with 5×10⁶ 92-1 uveal melanoma cells in 50% Matrigel. Tumors were grown to a mean of ~200 mm³, at which point mice were grouped and dosing was initiated. Mice were dosed once daily by oral gavage with vehicle (20% 2-Hydroxypropyl-8-Cyclodextrin) or increasing doses of Compound C. Tumor volumes and body weights were measured over the course of 3 weeks, and doses were adjusted by body weight to achieve the proper dose in terms of mg/kg. At this time, animals were sacrificed, and tumors were dissected and imaged.

Figure 11:
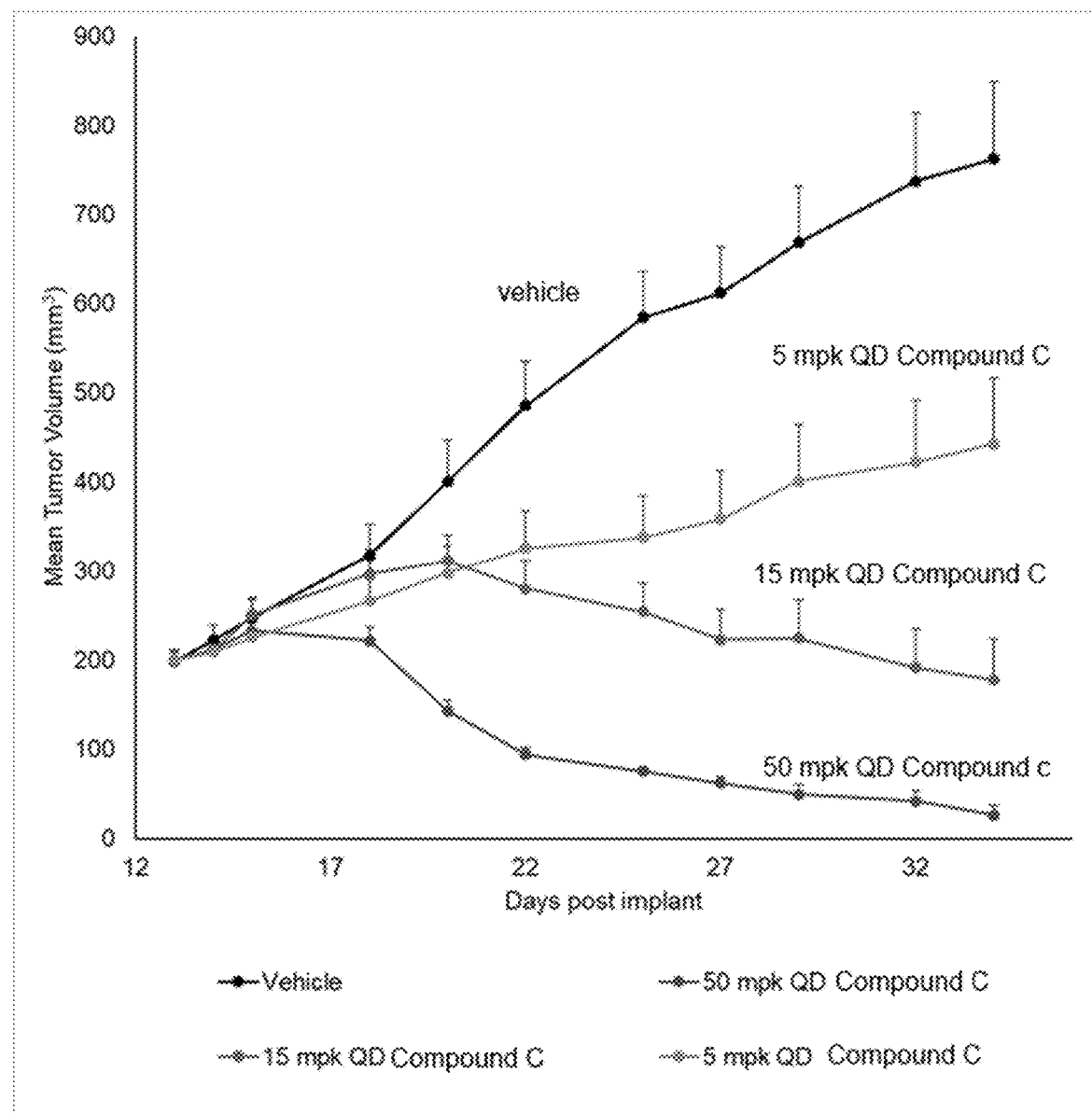
FIG. 11 is a graph illustrating inhibition of tumor growth in mice engrafted with uveal melanoma cell lines by a BRG1/BRM inhibitor (Compound C).
Figure 12:
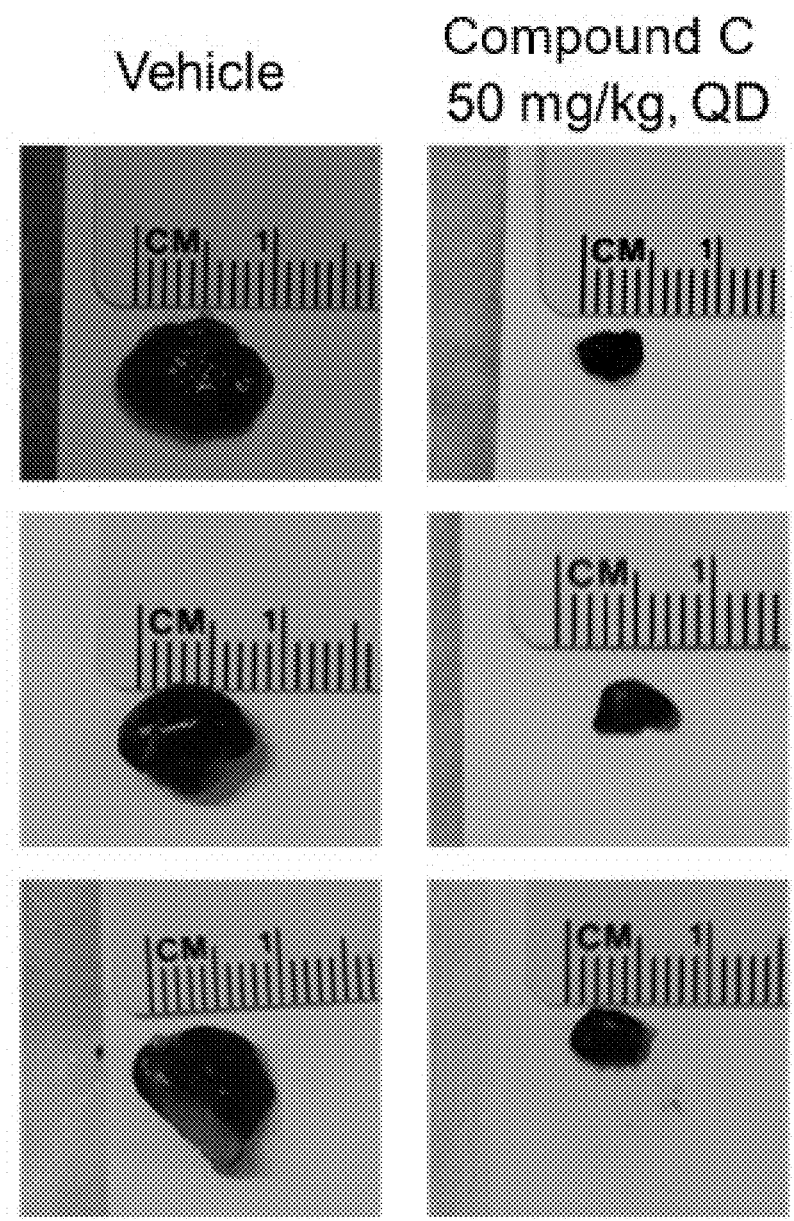
FIG. 12 is an illustration of the size of tumors from mice engrafted with uveal melanoma cell lines and dosed with a BRG1/BRM inhibitor (Compound C).
Figure 13:
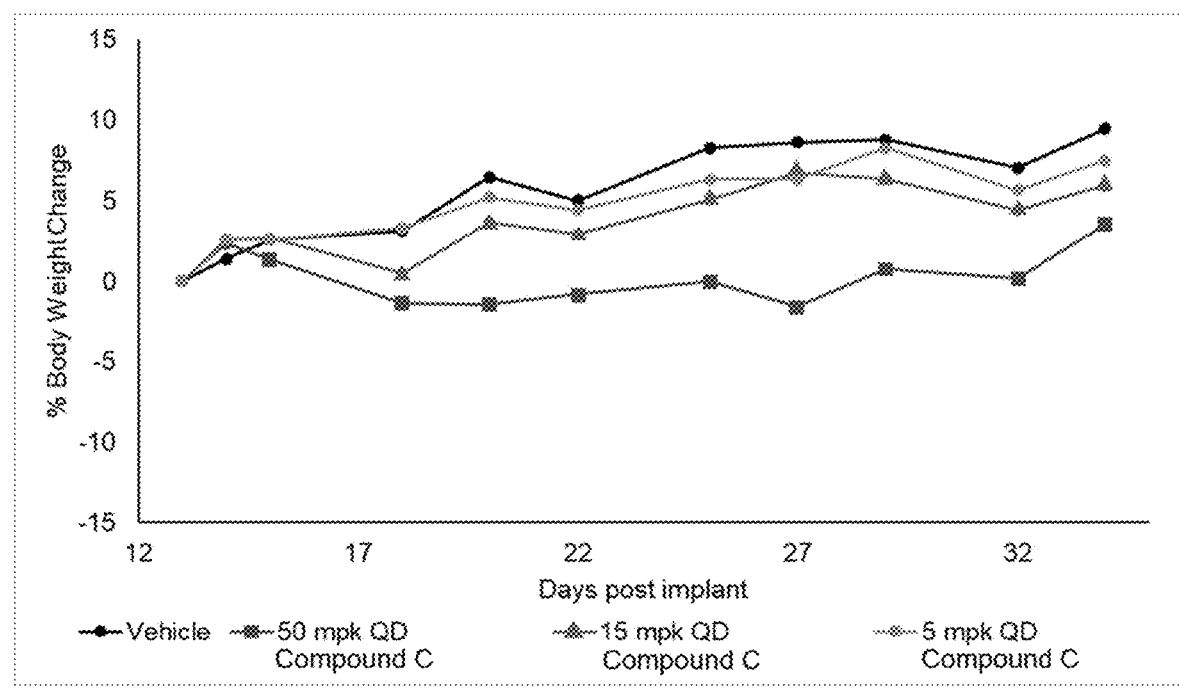
FIG. 13 is a graph illustrating body weight change of mice engrafted with uveal melanoma cell lines and dosed with a BRG1/BRM inhibitor (Compound C).

Results: As shown in FIG. 11 and FIG. 12, treatment with Compound C led to tumor growth inhibition in a dose-dependent manner with tumor regression observed at the highest (50 mg/kg) dose. As shown in FIG. 13, all treatments were well tolerated with no body weight loss observed (FIG. 13).

Example 17. Effects of BRG1/BRM ATPase Inhibition on the Growth of Uveal Melanoma and Hematological Cancer Cell Lines Procedure: Uveal melanoma cell lines (92-1, MEL202, MP41, MP38, MP46), prostate cancer cells (22RV1), acute leukemia cells (EOL1, THP1), and histocytic lymphoma cells (U937) were plated into 96 well plates with growth media (see Table 2). BRG1/BRM ATPase inhibitor, N—((S)-1-((4-(6-(cis-2,6-dimethylmorpholino)pyridin-2-yl)thiazol-2-yl)amino)-3-methoxy-1-oxopropan-2-yl)-1-(methylsulfonyl)-1H-pyrrole-3-carboxamide, was dissolved in DMSO and added to the cells in a concentration gradient from 0 to 2 µM (for uveal melanoma cell lines), or 0 to 1 µM (for other cell lines), at the time of plating. Cells were incubated at 37° C. for 3 days. After three days of treatment, cell growth was measured with Cell-titer glow (Promega), and luminescence was read on an Envision plate reader (Perkin Elmer).

Figure 14:
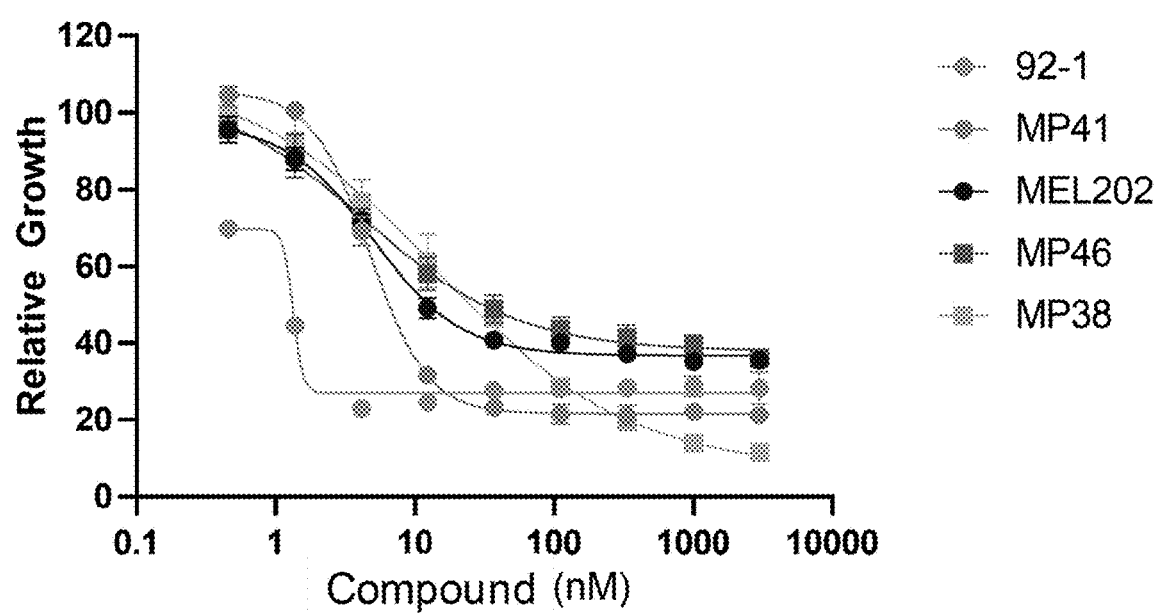
FIG. 14 is a graph illustrating inhibition of cell proliferation of several uveal melanoma cell lines by N—((S)-1-((4-(6-(cis-2,6-dimethylmorpholino)pyridin-2-yl)thiazol-2-yl)amino)-3-methoxy-1-oxopropan-2-yl)-1-(methylsulfonyl)-1H-pyrrole-3-carboxamide.

Results: As shown in FIG. 14, N—((S)-1-((4-(6-(cis-2,6-dimethylmorpholino)pyridin-2-yl)thiazol-2-yl)amino)-3-methoxy-1-oxopropan-2-yl)-1-(methylsulfonyl)-1H-pyrrole-3-carboxamide resulted in potent growth inhibition in all the cell lines. As shown in Table 3, measured absolute IC₅₀ values were below 350 nanomolar for all cell lines tested.

Table 3 lists the tested cell lines, growth media used, and absolute IC₅₀ values (nM) after 3 days of compound treatment.

TABLE 3

Cell Lines, Growth Media, and Absolute IC$_{50}$ values

| Cell Line | Source | Growth Media | Cancer Type | Absolute IC$_{50}$ (nM) |
|---|---|---|---|---|
| 22RV1 | ATCC | RPMI1640 + 10% FBS | Prostate | 29.7 |
| 92-1 | SIGMA | RPMI1640 + 10% FBS | Uveal melanoma | 0.3 |
| EOL1 | DSMZ | RPMI1640 + 10% FBS | Acute myeloid leukemia | 75.5 |
| MEL202 | SIGMA | RPMI1640 + 10% FBS | Uveal melanoma | 62.3 |
| MP38 | ATCC | RPMI1640 + 20% FBS | Uveal melanoma | 31.5 |
| MP41 | ATCC | RPMI1640 + 20% FBS | Uveal melanoma | 11.8 |
| MP46 | ATCC | RPMI1640 + 20% FBS | Uveal melanoma | 112.6 |
| THP1 | ATCC | RPMI1640 + 10% FBS | Acute monocytic leukemia | 344.9 |
| U937 | ATCC | RPMI1640 + 10% FBS | Histiocytic lymphoma | 14.8 |

Example 18. BRG1/BRM ATPase Inhibition Causes Uveal Melanoma Tumor Growth Inhibition In Vivo Procedure: Nude mice (Envigo) were engrafted subcutaneously in the axillary region with 5×10⁶ 92-1 uveal melanoma cells in 50% Matrigel. Tumors were grown to a mean of ~200 mm³, at which point mice were grouped and dosing was initiated. Mice were dosed once daily by oral gavage with vehicle (20% 2-Hydroxypropyl-β-Cyclodextrin) or increasing doses of N—((S)-1-((4-(6-(cis-2,6-dimethylmorpholino)pyridin-2-yl)thiazol-2-yl)amino)-3-methoxy-1-oxopropan-2-yl)-1-(methylsulfonyl)-1H-pyrrole-3-carboxamide. Tumor volumes and body weights were measured over the course of 3 weeks, and doses were adjusted by body weight to achieve the proper dose in terms of mg/kg.

Figure 15:
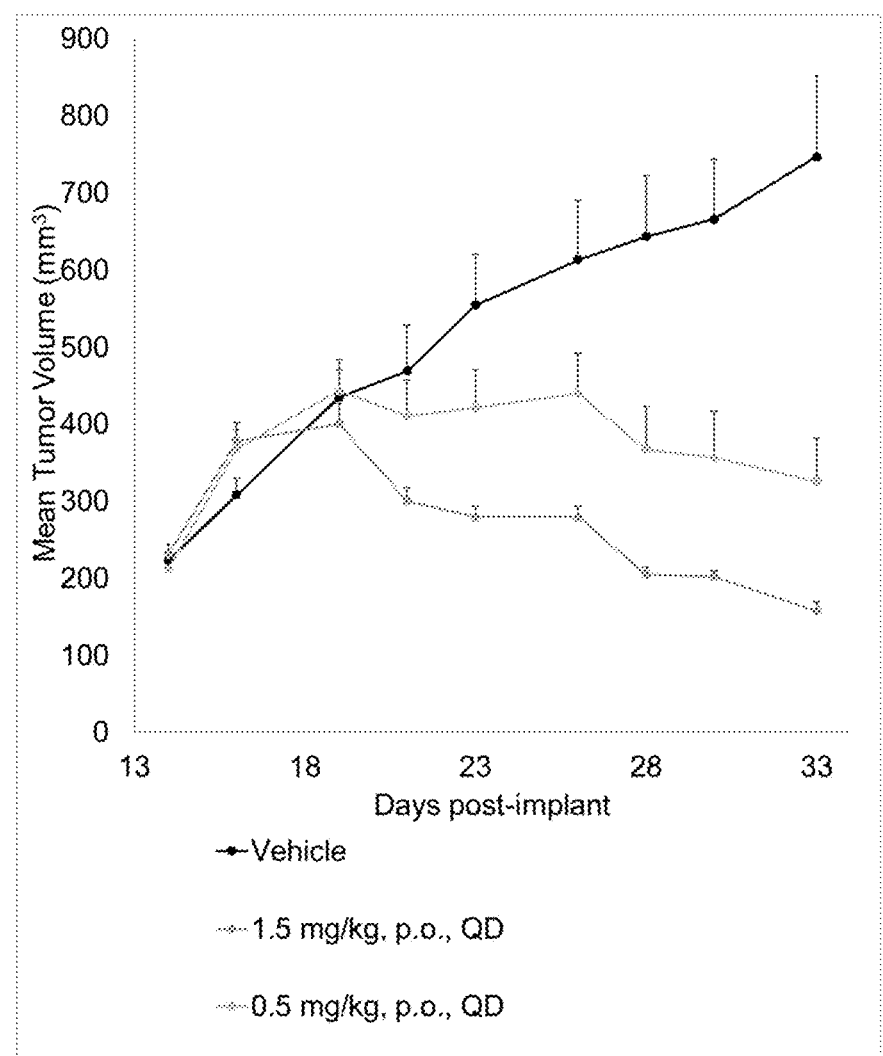
FIG. 15 is a graph illustrating inhibition of tumor growth in mice engrafted with uveal melanoma cell lines by N—((S)-1-((4-(6-(cis-2,6-dimethylmorpholino)pyridin-2-yl)thiazol-2-yl)amino)-3-methoxy-1-oxopropan-2-yl)-1-(methylsulfonyl)-1H-pyrrole-3-carboxamide.
Figure 16:
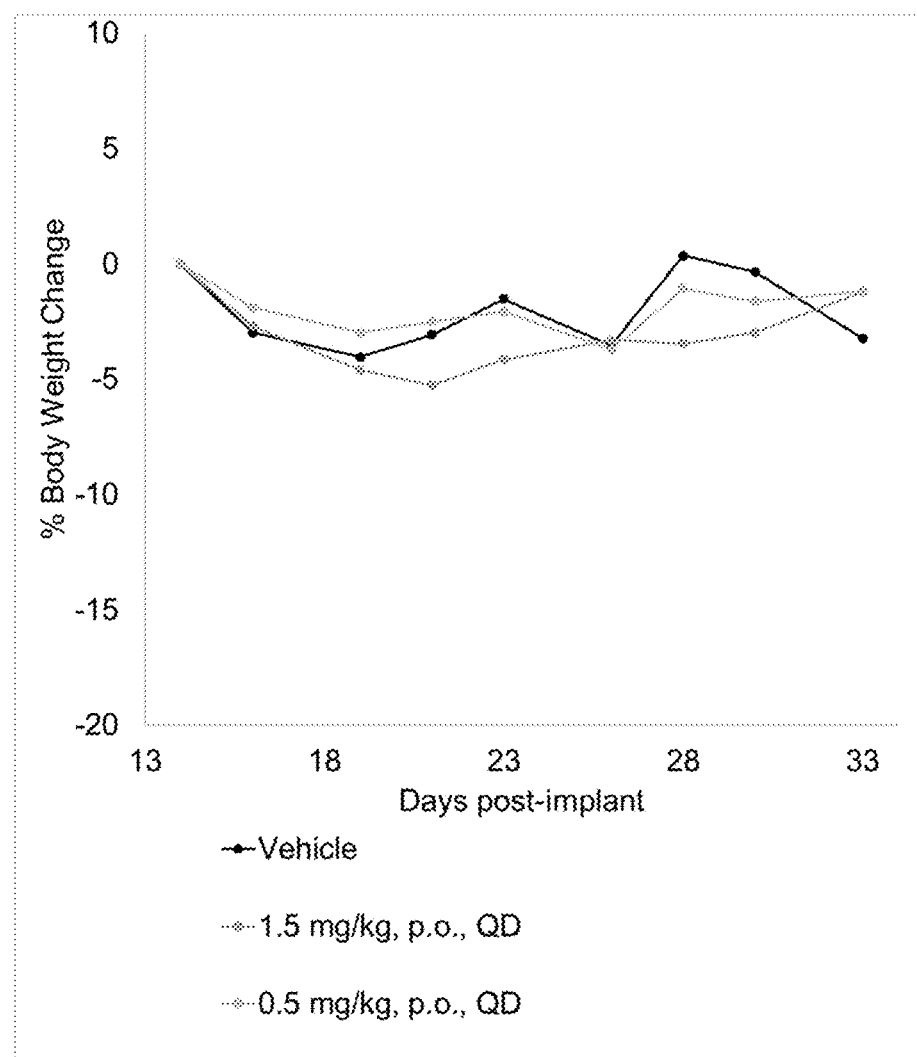
FIG. 16 is a graph illustrating body weight change of mice engrafted with uveal melanoma cell lines and dosed with N—((S)-1-((4-(6-(cis-2,6-dimethylmorpholino)pyridin-2- yl)thiazol-2-yl)amino)-3-methoxy-1-oxopropan-2-yl)-1-(methylsulfonyl)-1H-pyrrole-3-carboxamide.

Results: As shown in FIG. 15, treatment with N—((S)-1-((4-(6-(cis-2,6-dimethylmorpholino)pyridin-2-yl)thiazol-2-yl)amino)-3-methoxy-1-oxopropan-2-yl)-1-(methylsulfonyl)-1H-pyrrole-3-carboxamide led to tumor growth inhibition in a dose-dependent manner with tumor regression observed at the highest (1.5 mg/kg) dose. As shown in FIG. 16, all treatments were well tolerated based on % body weight change observed.

Other Embodiments

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

What is claimed is:

1. A compound having the structure:

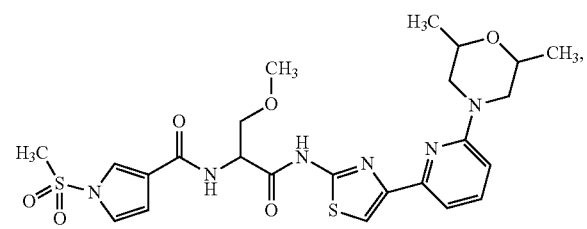 [SMILES: COCC(NC(=O)c1ccn(S(C)(=O)=O)c1)C(=O)Nc1nc(-c2cccc(N3CC(C)OC(C)C3)n2)cs1]

or a pharmaceutically acceptable salt thereof.

2. The compound of claim 1, wherein the compound has the structure:

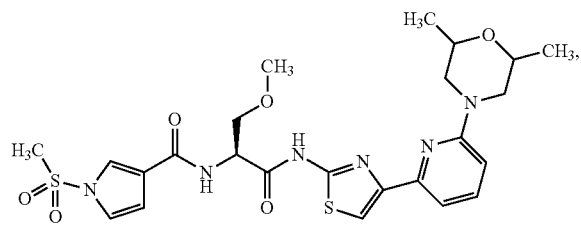 [SMILES: COC[C@H](NC(=O)c1ccn(S(C)(=O)=O)c1)C(=O)Nc1nc(-c2cccc(N3CC(C)OC(C)C3)n2)cs1]

or a pharmaceutically acceptable salt thereof.

3. The compound of claim 2, wherein the compound has the structure:

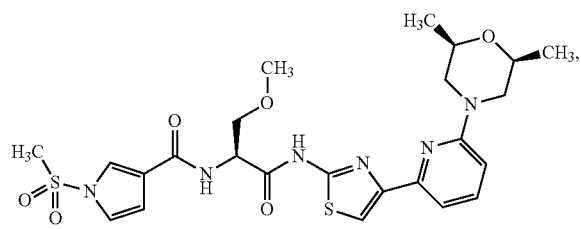 [SMILES: COC[C@H](NC(=O)c1ccn(S(C)(=O)=O)c1)C(=O)Nc1nc(-c2cccc(N3C[C@@H](C)O[C@@H](C)C3)n2)cs1]

or a pharmaceutically acceptable salt thereof.

4. The compound of claim 1, wherein the compound has the structure:

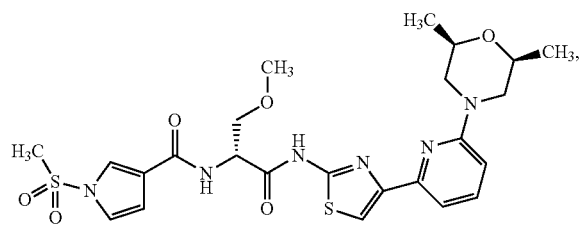 [SMILES: COC[C@@H](NC(=O)c1ccn(S(C)(=O)=O)c1)C(=O)Nc1nc(-c2cccc(N3C[C@@H](C)O[C@@H](C)C3)n2)cs1]

or a pharmaceutically acceptable salt thereof.

5. A compound having the structure:

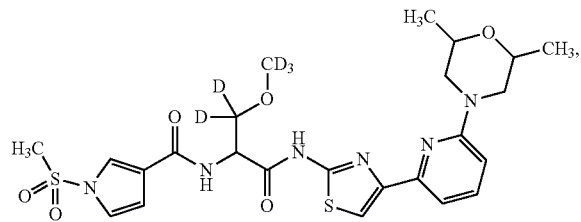 [SMILES: [2H]C([2H])([2H])OC([2H])([2H])C(NC(=O)c1ccn(S(C)(=O)=O)c1)C(=O)Nc1nc(-c2cccc(N3CC(C)OC(C)C3)n2)cs1]

or a pharmaceutically acceptable salt thereof.

6. A pharmaceutical composition comprising a compound of claim 1 and a pharmaceutically acceptable excipient.

7. A method of treating cancer in a subject in need thereof, the method comprising administering to the subject an effective amount of a compound of claim 1.

8. The method of claim 7, wherein the cancer is non-small cell lung cancer, colorectal cancer, bladder cancer, cancer of unknown primary, glioma, breast cancer, melanoma, non-melanoma skin cancer, endometrial cancer, esophagogastric cancer, esophageal cancer, pancreatic cancer, hepatobiliary cancer, soft tissue sarcoma, ovarian cancer, head and neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, adrenocortical carcinoma, appendiceal cancer, small bowel cancer, penile cancer, bone cancer, or hematologic cancer.

9. The method of claim 8, wherein the cancer is melanoma.

10. The method of claim 9, wherein the melanoma is uveal melanoma.

11. The method of claim 7, wherein the cancer is hematologic cancer.

12. The method of claim 11, wherein the hematologic cancer is acute myeloid leukemia.

13. The method of claim 7, wherein the cancer expresses BRG1 and/or BRM protein.

14. The method of claim 7, wherein the cancer has, or has been determined to have, a KRAS mutation, a mutation in GNAQ, a mutation in GNA11, a mutation in PLCB4, a mutation in CYSLTR2, a mutation in BAP1, a mutation in SF3B1, a mutation in EIF1AX, a TFE3 translocation, a TFEB translocation, a MITF translocation, an EZH2 mutation, a SUZ12 mutation, and/or an EED mutation.

15. The method of claim 7, wherein the cancer is metastatic.

16. The method of claim 7, wherein the cancer is resistant to, or failed to respond to prior treatment with, an anticancer therapy.

17. The method of claim 7, wherein the method further comprises administering to the subject an anticancer therapy.

18. A method for treating a viral infection in a subject in need thereof, the method comprising administering to the subject an effective amount of a compound of claim 1.

* * * * *